US012800777B2

(12) United States Patent
Hoshina et al.

(10) Patent No.: US 12,800,777 B2
(45) Date of Patent: Nov. 17, 2026

(54) SYSTEM COMPRISING A RADIATION DETECTION APPARATUS INCLUDING A PLURALITY OF SENSOR UNITS AND A COUPLING MEMBER, AND MANUFACTURING METHOD THEREOF

(71) Applicant: CANON KABUSHIKI KAISHA, Tokyo (JP)

(72) Inventors: Tomohiro Hoshina, Kanagawa (JP); Yoshito Sasaki, Tokyo (JP); Takaaki Gonda, Kanagawa (JP); Yoshitaka Otsubo, Kanagawa (JP); Akira Kida, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 195 days.

(21) Appl. No.: 18/773,741

(22) Filed: Jul. 16, 2024

(65) Prior Publication Data

US 2025/0044465 A1 Feb. 6, 2025

(30) Foreign Application Priority Data

Aug. 4, 2023 (JP) ................................ 2023-128000
Aug. 4, 2023 (JP) ................................ 2023-128003
Mar. 26, 2024 (JP) ................................ 2024-049991

(51) Int. Cl.
*A61B 6/03* (2006.01)
*A61B 6/42* (2024.01)
(Continued)

(52) U.S. Cl.
CPC .............. *G01T 1/24* (2013.01); *A61B 6/4241* (2013.01); *A61B 6/4266* (2013.01);
(Continued)

(58) Field of Classification Search
CPC ........... A61B 6/032; A61B 6/035; A61B 6/42; A61B 6/4208; A61B 6/4233;
(Continued)

(56) References Cited

U.S. PATENT DOCUMENTS 5,668,851 A * 9/1997 Dobbs .................. A61B 6/4291 378/7
6,396,898 B1 * 5/2002 Saito .................... G01N 23/046 378/19

(Continued)

FOREIGN PATENT DOCUMENTS

JP 2003-329778 A 11/2003
JP 2008-298556 A 12/2008
JP 2012-37281 A 2/2012

*Primary Examiner* — Allen C. Ho
(74) *Attorney, Agent, or Firm* — Venable LLP

(57) ABSTRACT

A radiation detection apparatus includes a plurality of unit structures each having a semiconductor layer that converts radiation into a charge, the unit structures being arranged to form an array, and a coupling member that couples two of the unit structures adjacent to each other in the array. The coupling member is formed from a material capable of being used as a vapor deposition material. Each of the plurality of unit structures further includes a mounting board on which is mounted an integrated circuit that processes a signal based on the charge obtained by the semiconductor layer.

20 Claims, 23 Drawing Sheets

(51) Int. Cl.

| | |
|---|---|
| ***G01T 1/24*** | (2006.01) |
| ***G01T 1/29*** | (2006.01) |
| ***H10F 39/00*** | (2025.01) |
| ***H10F 39/18*** | (2025.01) |

(52) U.S. Cl.
CPC ............ *A61B 6/4275* (2013.01); *G01T 1/243* (2013.01); *G01T 1/244* (2013.01); *G01T 1/2985* (2013.01); *H10F 39/1892* (2025.01); *H10F 39/1895* (2025.01); *H10F 39/811* (2025.01)

(58) Field of Classification Search
CPC ... A61B 6/4241; A61B 6/4266; A61B 6/4275; A61B 6/482; G01T 1/24; G01T 1/243; G01T 1/244; G01T 1/247; G01T 1/249; G01T 1/29; G01T 1/2914; G01T 1/2921; G01T 1/2928; G01T 1/2985
USPC ........................ 378/19, 62, 98.9; 250/370.09
See application file for complete search history.

(56) References Cited

U.S. PATENT DOCUMENTS

| | | | | |
|---|---|---|---|---|
| 6,510,195 | B1 * | 1/2003 | Chappo | G01T 1/2019 250/370.09 |
| 6,587,538 | B2 * | 7/2003 | Igarashi | A61B 6/4291 378/19 |
| 6,671,345 | B2 * | 12/2003 | Vrettos | A61B 6/032 378/19 |
| 6,917,664 | B2 * | 7/2005 | Chappo | A61B 6/032 378/19 |
| 6,982,423 | B2 * | 1/2006 | Elgali | G01T 1/1648 250/370.11 |
| 7,190,759 | B2 * | 3/2007 | Ratzmann | A61B 6/035 378/19 |
| 7,202,482 | B2 * | 4/2007 | Yokoi | G01T 1/2928 250/370.09 |
| 7,235,790 | B2 * | 6/2007 | Hoge | G01T 1/1648 250/370.11 |
| 7,297,955 | B2 * | 11/2007 | Amemiya | G01T 1/2928 250/370.09 |
| 7,492,857 | B2 * | 2/2009 | Yasunaga | A61B 6/032 378/19 |
| 7,511,277 | B2 * | 3/2009 | Ueno | A61B 6/037 250/363.04 |
| 7,525,097 | B2 * | 4/2009 | Dorscheid | A61B 6/4291 250/370.11 |
| 8,829,446 | B2 * | 9/2014 | Abenaim | G01T 1/2985 250/363.01 |
| 8,866,098 | B2 * | 10/2014 | Hayatsu | G01T 1/20 250/370.09 |
| 9,322,938 | B2 * | 4/2016 | Kämmerer | G01T 1/2985 |
| 10,307,117 | B2 * | 6/2019 | Park | A61B 6/4266 |
| 11,061,150 | B2 * | 7/2021 | Ye | A61B 6/4266 |
| 11,067,707 | B2 * | 7/2021 | Crestani | G01T 1/243 |
| 11,166,685 | B2 * | 11/2021 | Takayasu | A61B 6/4266 |
| 11,474,050 | B2 * | 10/2022 | Read | A61B 6/4266 |
| 11,510,637 | B2 * | 11/2022 | Nishijima | A61B 6/032 |
| 11,567,016 | B2 * | 1/2023 | Onouchi | G01N 23/046 |
| 12,189,066 | B2 * | 1/2025 | Onouchi | G01T 1/247 |
| 12,405,231 | B2 * | 9/2025 | Onouchi | A61B 6/4241 |
| 12,419,596 | B2 * | 9/2025 | Fan | A61B 6/4241 |
| 12,468,054 | B2 * | 11/2025 | Ayukawa | A61B 6/4241 |
| 12,560,728 | B2 * | 2/2026 | Iniewski | G01T 1/241 |
| 12,588,879 | B2 * | 3/2026 | Nakagawa | A61B 6/4241 |
| 2024/0138787 | A1 | 5/2024 | Nakagawa et al. | |

* cited by examiner

SYSTEM COMPRISING A RADIATION DETECTION APPARATUS INCLUDING A PLURALITY OF SENSOR UNITS AND A COUPLING MEMBER, AND MANUFACTURING METHOD THEREOF

BACKGROUND OF THE INVENTION

Field of the Invention

The present invention relates to a radiation detection apparatus, a manufacturing method thereof, and a system.

Description of the Related Art

A radiation detection apparatus having a semiconductor layer that converts radiation into a charge has been proposed. In some radiation detection apparatuses, a large sensor surface is formed by arranging a plurality of sensor units in a one- or two-dimensional array. Japanese Patent Laid-Open No. 2012-37281 describes a radiation detection apparatus in which substrates on which semiconductor elements are mounted are inserted into a slit member to align a plurality of the substrates. Japanese Patent Laid-Open No. 2008-298556 describes a radiation detector in which an adhesive or a bonding agent that absorbs X-rays is disposed in a gap between adjacent ones of a plurality of modules in which a plurality of X-ray detection elements are arranged one- or two-dimensionally. Japanese Patent Laid-Open No. 2003-329778 describes a technique for coating each side surface of a plurality of X-ray detection elements with an insulating material. Variations in the heights of the plurality of semiconductor layers that detect radiation can reduce the accuracy of radiation detection by the radiation detection apparatus. In addition, radiation entering the gaps between the plurality of semiconductor layers is not detected, and thus if the gaps are large, the accuracy of the radiation detection by the radiation detection apparatus can drop.

SUMMARY OF THE INVENTION

Some aspects of the present disclosure provide a technique for improving the accuracy of radiation detection. According to an embodiment, a radiation detection apparatus comprising: a plurality of unit structures each having a semiconductor layer that converts radiation into a charge, the unit structures being arranged to form an array; and a coupling member that couples two of the unit structures adjacent to each other in the array, wherein the coupling member is formed from a material capable of being used as a vapor deposition material, and each of the plurality of unit structures further includes a mounting board on which is mounted an integrated circuit that processes a signal based on the charge obtained by the semiconductor layer is provided.

Further features of the present invention will become apparent from the following description of exemplary embodiments with reference to the attached drawings.

DESCRIPTION OF THE EMBODIMENTS

Figure 1:
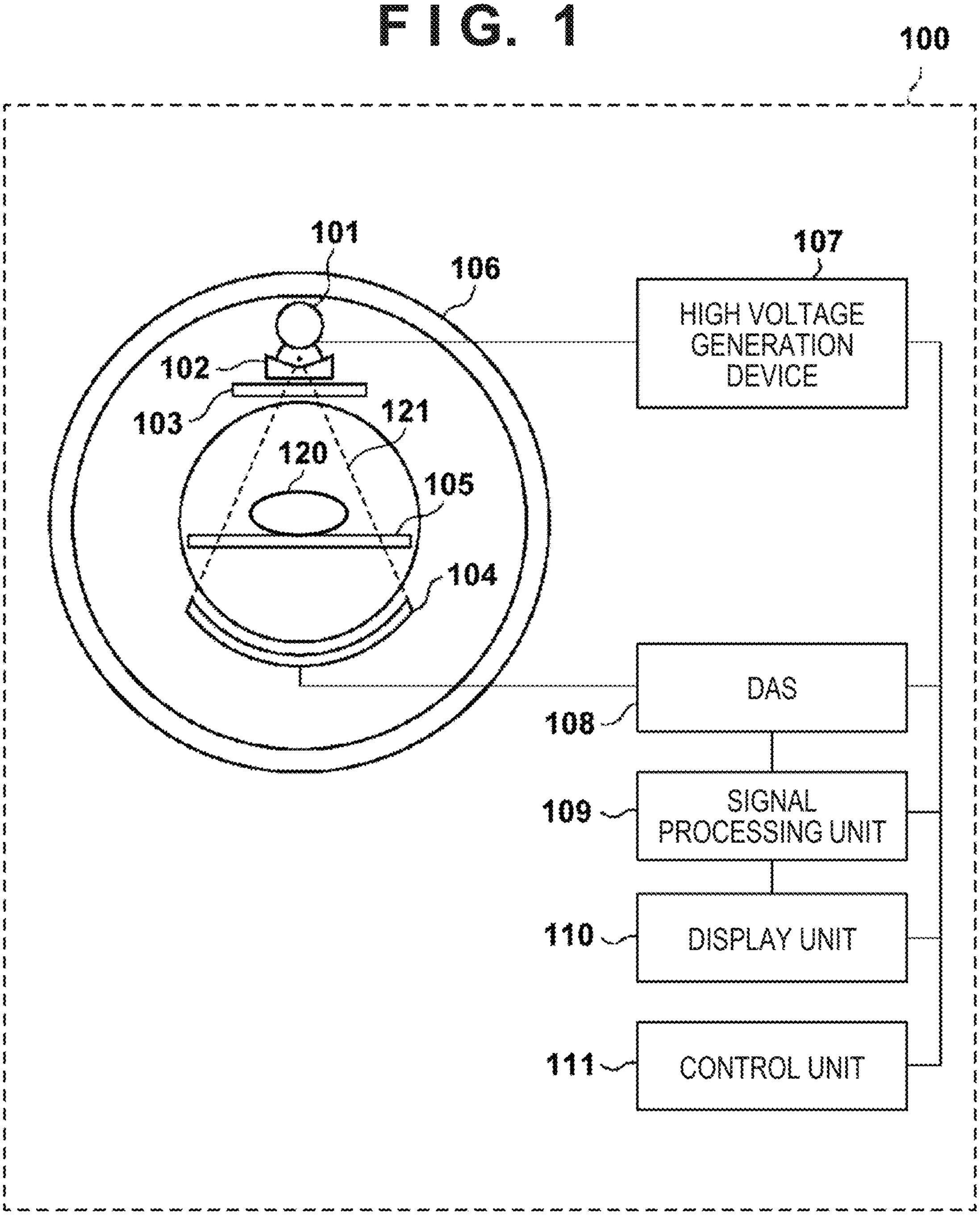
FIG. 1 is a block diagram illustrating an example of the configuration of a CT apparatus according to some embodiments.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

In addition to α-rays, β-rays, γ-rays, and the like, which are beams created by particles (including photons) emitted as a result of radiation decay, "radiation" in the following descriptions can also include beams with the equivalent or higher energy, such as X-rays, particle beams, cosmic rays, and the like, for example. In this application, photons such as X-rays and γ-rays and particles such as β-rays and α-rays may be described collectively as "radiation photons".

An example of the configuration of a computed tomography (CT) apparatus 100 according to some embodiments will be described with reference to the block diagram in FIG. 1. The CT apparatus 100 may include a radiation generation unit 101, a wedge 102, a collimator 103, a radiation detection apparatus 104, a top plate 105, a rotating frame 106, a high voltage generation device 107, a data acquisition system (DAS) 351, a signal processing unit 109, a display unit 110, and a control unit 111. This configuration is merely an example, and the CT apparatus 100 may have a different configuration.

The CT apparatus 100 may be an apparatus capable of performing photon counting CT. In other words, the CT apparatus 100 described in the following embodiment may be an apparatus capable of reconstructing CT image data with a high SN ratio by counting radiation transmitted through a subject using a photon counting-type radiation detection apparatus 104. The radiation detection apparatus 104 described in the following embodiment may also be a direct conversion-type detector that directly converts radiation photons into a charge proportional to the energy thereof.

The radiation generation unit 101 emits radiation toward the radiation detection apparatus 104. The radiation generation unit 101 is constituted by, for example, a vacuum tube that generates X-rays. A high voltage and filament current are supplied to the vacuum tube of the radiation generation unit 101 from the high voltage generation device 107. X-rays are produced when thermoelectrons are emitted from a cathode (filament) toward an anode (target). The wedge 102 is a filter that adjusts the amount of radiation 121 emitted from the radiation generation unit 101. The wedge 102 attenuates the radiation dose such that the radiation 121 emitted from the radiation generation unit 101 to a subject 120 has a predetermined distribution. The collimator 103 is constituted by a lead plate or the like that narrows the irradiation range of radiation transmitted through wedge 102. The radiation 121 generated by the radiation generation unit 101 is formed into a cone beam shape through the collimator 103 and emitted onto the subject 120 on the top plate 105.

The radiation detection apparatus 104 detects the radiation 121 passing through the subject 120 from the radiation generation unit 101, and outputs a signal corresponding to the radiation dose to the DAS 108. The subject 120 may be a living organism (e.g., a human or an animal), or an inanimate object.

Each time a radiation photon is incident on the radiation detection apparatus 104, a signal through which the energy value of the radiation photon can be measured may be output. Radiation photons are, for example, radiation photons emitted from the radiation generation unit 101 and transmitted through the subject 120. The radiation detection apparatus 104 has a plurality of detection elements that output one pulse of an electrical signal (an analog signal) each time a radiation photon is incident. By counting the number of electrical signals (pulses), the number of radiation photons incident on each detection element can be counted. Additionally, by performing arithmetic processing on the signal, the energy value of the radiation photon that produced the output of the signal can be measured.

The detection element mentioned above may be, for example, a semiconductor detection element such as CdTe (cadmium telluride) or CdZnTe (cadmium zinc telluride), with electrodes disposed thereon. In other words, the radiation detection apparatus 104 is a direct conversion-type detector that converts incident radiation photons directly into electrical signals. The radiation detection apparatus 104 has a plurality of the stated detection elements, as well as a plurality of Application Specific Integrated Circuits (ASICs) which are connected to the detection elements and which count the radiation photons detected by the corresponding detection elements. Each ASIC counts the number of radiation photons incident on the detection element by distinguishing the individual charges output by the detection element. The ASIC also measures the energy of the counted X-ray photons by performing arithmetic processing based on the magnitudes of the individual charges. Furthermore, the ASIC outputs the result of counting the radiation photons as digital data to the DAS 108.

The DAS 108 generates detection data based on the results of the counting processing input from the radiation detection apparatus 104. The detection data is a sinogram, for example. The sinogram is data that arranges the results of the processing for counting the photons incident on each detection element at each location of the radiation generation unit 101. The sinogram is data in which the results of the counting processing are arranged in a two-dimensional Cartesian coordinate system that takes the view direction and the channel direction as axes. The DAS 108 generates sinograms, for example, in units of columns in the slice direction in the radiation detection apparatus 104. The result of the counting processing is data that allocates a number of radiation photons for each of energy bins. For example, the DAS 108 counts photons derived from the radiation emitted from the radiation generation unit 101 and transmitted through the subject 120 (radiation photons) and distinguishes the energy of the counted radiation photons, which is the result of the counting processing. The DAS 108 is implemented by a processor, for example.

The rotating frame 106 is circular and capable of rotating. The radiation generation unit 101 (the wedge 102, the collimator 103) and the radiation detection apparatus 104 are disposed within the rotating frame 106 on opposite sides of each other with respect to the top plate 105. The radiation generation unit 101 and the radiation detection apparatus 104 are capable of rotating with the rotating frame 106.

The high voltage generation device 107 includes a booster circuit, and outputs a high voltage to the radiation generation unit 101. For example, the high voltage generation device 107 has electrical circuits such as a transformer, a rectifier, and the like, a high voltage generation unit that generates a high voltage to be applied to the radiation generation unit 101, and a radiation control unit that controls an output voltage according to the radiation generated by the radiation generation unit 101. The high voltage generation unit may be a transformer type or an inverter type. The high voltage generation device 107 may be provided in the rotating frame 106, or in a fixed frame (not shown). The DAS 108 includes an amplification circuit and an analog/digital (A/D) conversion circuit, and outputs signals from the radiation detection apparatus 104 as digital data to the signal processing unit 109.

The signal processing unit 109 processes signals output from the radiation detection apparatus 104. The signal processing unit 109 may include a central processing unit (CPU), a read-only memory (ROM), and a random access memory (RAM). The display unit 110 includes a flat-panel display device or the like, and is capable of displaying radiological images. The control unit 111 includes a CPU, a ROM, a RAM, and the like, and controls the operations of the CT apparatus 100 as a whole. For example, the control unit 111 has processing circuitry including a CPU and the like, and drive mechanisms such as motors and actuators. The control unit 111 receives input signals from an input interface and controls the operations of a gantry and a subject table. For example, the control unit 111 controls the rotation of the rotating frame 106, the tilt of the gantry, and the movement of the subject table and the top panel. To give one example, as control that tilts the gantry, the control unit 111 rotates the rotating frame 106 about an axis parallel to an X-axis direction according to tilt angle information that is input. The control unit 111 may be provided in the gantry or in a console device.

The input interface accepts various input operations from an operator, converts the accepted input operations into electrical signals, and outputs the electrical signals to the control unit 111. For example, the input interface accepts, from the operator, input operations such as reconstruction conditions for reconstructing CT image data, image processing conditions for generating a post-processing image from the CT image data, and the like. For example, the input interface is realized by a mouse, a keyboard, a trackball, switches, buttons, a joystick, a touchpad through which input operations are made by touching an operating surface, a touchscreen in which a display screen and a touchpad are integrated, a non-contact input circuit that uses a photosensor, an audio input circuit, or the like. The input interface may be provided in the gantry. Alternatively, the input interface may be constituted by a tablet terminal or the like capable of communicating wirelessly with the main body of the console device. Furthermore, the input interface is not limited to an interface that includes physical operating components such as a mouse, a keyboard, or the like. For example, electrical signal processing circuitry that receives an electrical signal corresponding to an input operation from an external input device provided separate from the console device, and outputs the electrical signal to the control unit 111, is also an example of the input interface.

The signal processing unit 109 may have a pre-processing function. Using the pre-processing function, the signal processing unit 109 can generate projection data by performing pre-processing such as logarithmic conversion processing, offset correction processing, inter-channel sensitivity correction processing, beam hardening correction, and the like on the detection data output from the DAS 108. The signal processing unit 109 may also have a reconstruction processing function. Using the reconstruction processing function, the signal processing unit 109 can generate CT image data by performing reconstruction processing using filtered back projection, a successive approximation reconstruction, or the like on the projection data generated by the pre-processing function. Additionally, using the reconstruction processing function, the signal processing unit 109 can store the reconstructed CT image data in a memory.

The projection data generated from the counting results obtained in photon counting CT contains information on the energy of X-rays attenuated by passing through the subject 120. As such, the signal processing unit 109 can reconstruct the CT image data of a specific energy component, for example, by using the reconstruction processing function. The signal processing unit 109 can also reconstruct the CT image data of each of a plurality of energy components, for example, by using the reconstruction processing function. Furthermore, using the reconstruction processing function, the signal processing unit 109 can, for example, assign a color according to the energy component to each pixel in CT image data indicating energy components, and generate image data in which a plurality of pieces of CT image data colored according to the energy components are superimposed on each other. The signal processing unit 109 can also generate image data through which a substance can be identified using, for example, the K-absorption edge unique to that substance, using the reconstruction processing function. Monochromatic X-ray image data, density image data, effective atomic number image data, and the like can be given as other types of image data generated by the signal processing unit 109 using the reconstruction processing function.

To reconstruct CT image data, 360° of projection data around the entire periphery of the subject is required, and for the half-scan method, projection data for 180° plus the fan angle is required. Either reconstruction method can be applied to the present embodiment. To simplify the descriptions, the following will assume that a reconstruction method which reconstructs the data using 360° of projection data around the entire periphery of the subject (full-scan reconstruction) is used.

The signal processing unit 109 may have an image processing function. Using the image processing function, the signal processing unit 109 can use a publicly-known method to convert the CT image data generated by the reconstruction processing function into image data such as a tomographic image of a desired cross-section, a three-dimensional image generated through rendering processing, or the like based on an input operation received from the operator through the input interface. Additionally, using the image processing function, the signal processing unit 109 can store the converted image data in a memory.

The control unit 111 may have a scan control function. The control unit 111 controls CT scanning performed through the gantry using a scan control function. For example, the control unit 111 controls processing for collecting counting results in the gantry by controlling the operations of the high voltage generation device 107, the radiation detection apparatus 104, the DAS 108, and a subject table driving device, using the scan control function. In one example, the control unit 111 controls processing for collecting projection data in imaging that collects positioning images (scanography images) and main imaging (scanning) that collects images for diagnosis, respectively, using the scan control function. The control unit 111 may have a display control function. The control unit 111 can control various types of image data stored in the memory to be displayed in the display unit 110, which is a display or the like, using the display control function.

Figure 2:
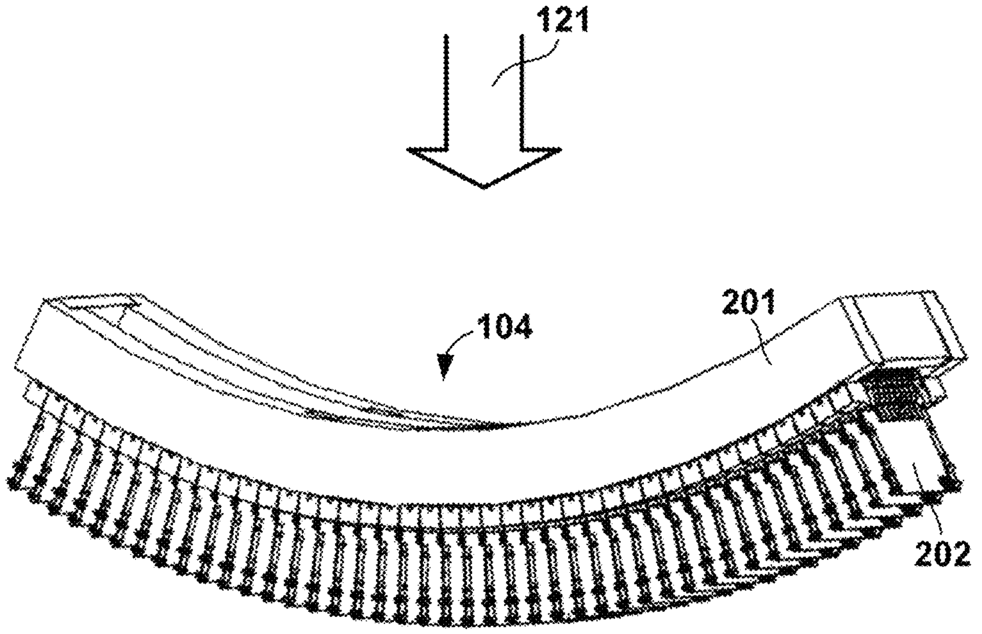
FIG. 2 is a perspective view illustrating an example of the configuration of a radiation detection apparatus according to some embodiments.

An example of the configuration of the radiation detection apparatus 104 will be described with reference to the perspective view in FIG. 2. This configuration is merely an example, and the radiation detection apparatus 104 may have a different configuration. The radiation detection apparatus 104 includes a base 201 and a plurality of sensor modules 202. The base 201 has an arc shape that is concave with respect to the radiation 121. The plurality of sensor modules 202 are fixed, side by side, to the curved surface of the base 201 along the circumferential direction thereof. The base 201 is fixed to the rotating frame 106.

Figure 3:
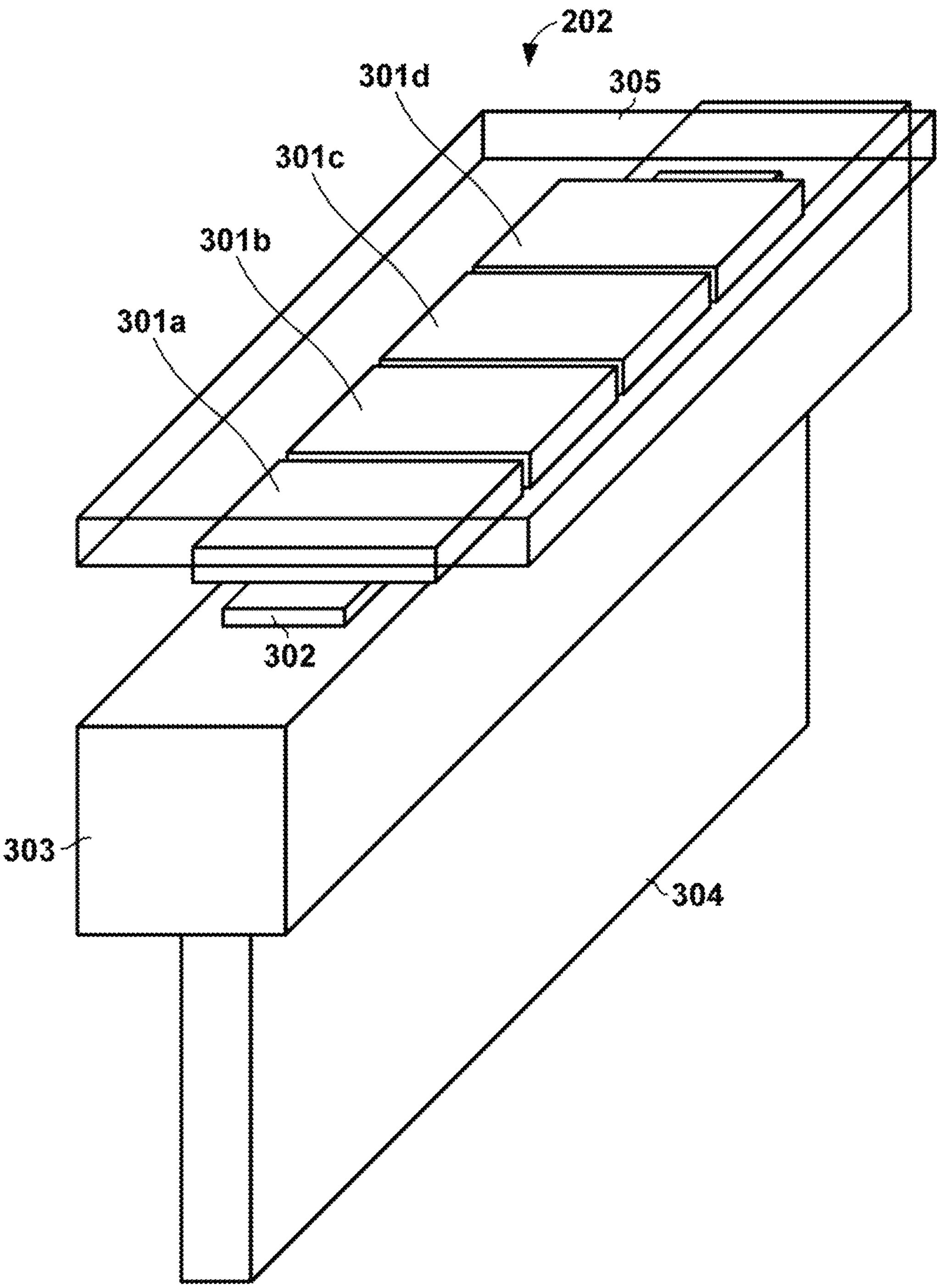
FIG. 3 is a schematic perspective view illustrating an example of the configuration of a sensor module according to some embodiments.

An example of the configuration of the sensor module 202 will be described with reference to the perspective view in FIG. 3. This configuration is merely an example, and the sensor module 202 may have a different configuration. The plurality of sensor modules 202 included in the radiation detection apparatus 104 may all have the configuration illustrated in FIG. 3. The sensor module 202 may include a plurality of sensor units 301*a* to 301*d*, a heat dissipation member 302, a frame 303, and a circuit board 304. In the following descriptions, the plurality of sensor units 301*a* to 301*d* will be referred to collectively as a "sensor unit 301". The descriptions of the sensor unit 301 may be applied to each of the plurality of sensor units 301*a* to 301*d*.

The sensor unit 301 generates a signal according to radiation incident on the sensor unit 301. The sensor unit 301 and the circuit board 304 are connected by a cable (not shown; for example, a flexible cable). The signal generated by the sensor unit 301 is read out to the DAS 108 through the circuit board 304. The plurality of sensor units 301 are arranged in the direction in which the frame 303 extends. In the example illustrated in FIG. 3, one sensor module 202 includes four sensor units 301, but the number of sensor units is not limited to this example. Furthermore, in the example illustrated in FIG. 3, the four sensor units 301 are arranged in one row, but the plurality of sensor units may be arranged in a plurality of rows.

The frame 303 is a rigid member for attaching the sensor unit 301. The frame 303 may be called a "mounting frame". The frame 303 may be formed from a metal, for example. The frame 303 functions as a support member that supports the sensor unit 301. The circuit board 304 is attached to the frame 303. The plurality of sensor units 301 and the circuit board 304 are located on opposite sides of the frame 303. The frame 303 is fixed to the base 201. For example, the frame 303 may be fixed to the base 201 mechanically using fasteners such as screws, or may be fixed to the base 201 chemically using an adhesive.

A substrate 305 is disposed in a position that covers the plurality of sensor units 301 provided in the sensor module 202. FIG. 3 illustrates the substrate 305 in a transparent manner for illustrative purposes. The substrate 305 may be disposed in common for the plurality of sensor units 301 included in one sensor module 202. For example, a single substrate 305 may be disposed for a single sensor module 202. Furthermore, the substrate 305 may be disposed in common for a plurality of sensor modules 202. For example, a single substrate 305 may be disposed for a radiation detection apparatus 104. The plurality of sensor units 301 are disposed so as to form an array. The plurality of sensor units 301 may configure a one-dimensional array, or may configure a two-dimensional array.

The substrate 305 is fixed to the frame 303. The substrate 305 may be fixed directly or indirectly to the frame 303. For example, the substrate 305 may be fixed to the frame 303 indirectly by fixing both the frame 303 and the substrate 305 to the base 201.

The heat dissipation member 302 is located between the frame 303 and a bottom surface 408 of each of the plurality of sensor units 301*a* to 301*d*. A single heat dissipation member 302 may be disposed in common for the plurality of sensor units 301. Instead, however, an individual heat dissipation member 302 may be disposed for each of the plurality of sensor units 301. For example, the heat dissipation member 302 may be wider than the bottom surfaces of the sensor units 301 in the short side direction of the frame 303. The heat dissipation member 302 transfers heat produced by the sensor units 301 to the frame 303. The heat dissipation member 302 may be formed from a metal, for example. However, the sensor module 202 need not include the heat dissipation member 302. In this case, heat produced by the sensor units 301 is transferred directly to the frame 303.

Figure 4:
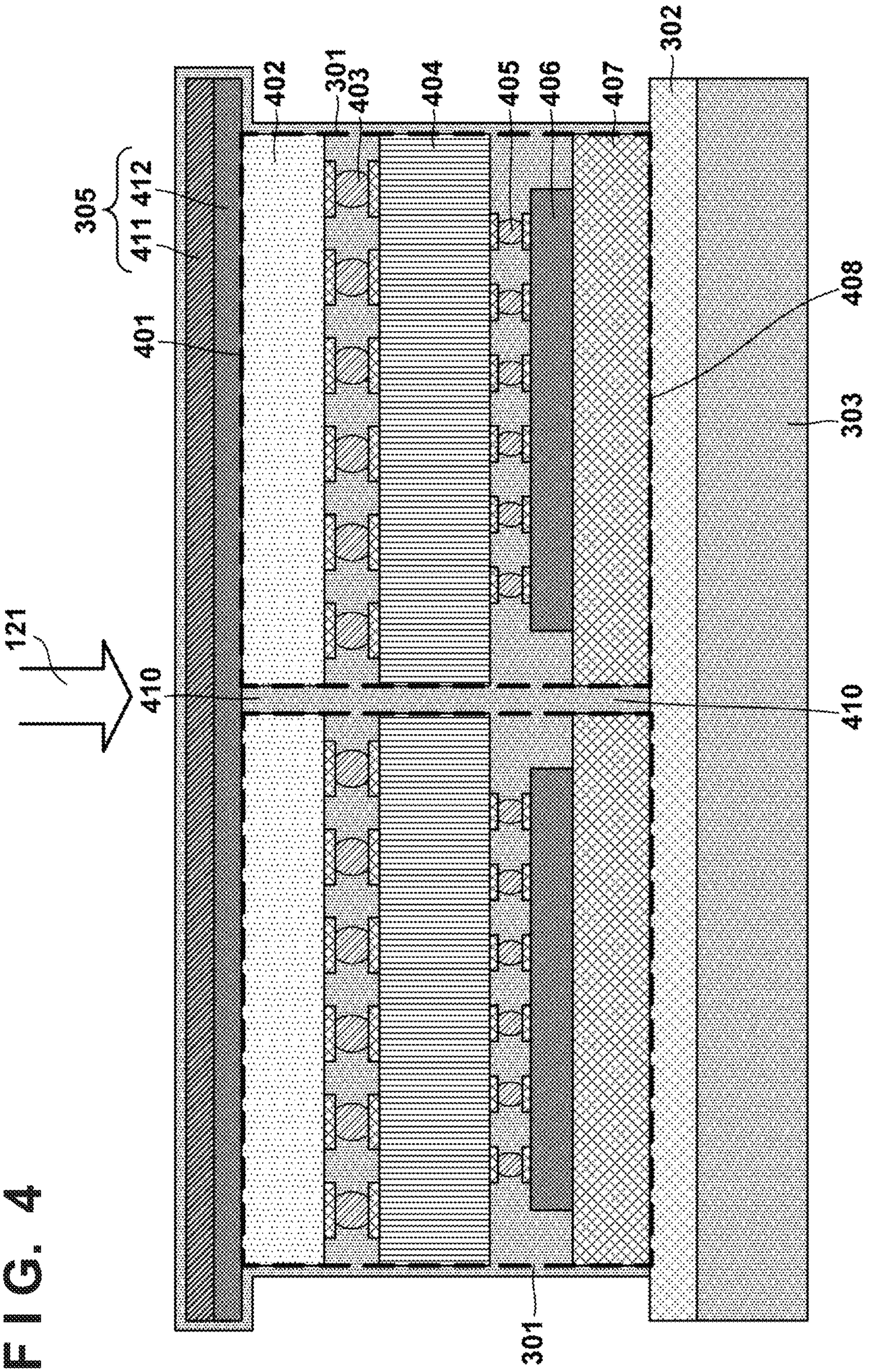
FIG. 4 is a cross-sectional view illustrating an example of the configuration of a sensor unit according to some embodiments.

An example of the configuration of the sensor unit 301 will be described with reference to the cross-sectional view in FIG. 4. This configuration is merely an example, and the sensor unit 301 may have a different configuration. The sensor unit 301 may include a semiconductor layer 402, an interposer 404, an integrated circuit 406, and a mounting board 407. In the following descriptions, the surface of each member on the upper side in the figures will be referred to as a "top surface", and the surface on the lower side in the figures will be referred to as a "bottom surface". The sensor unit 301 has a top surface 401 located on a radiation incidence side and the bottom surface 408, which is located on the side opposite from the top surface 401. FIG. 4 illustrates only two sensor units 301 adjacent to each other in the array, among the plurality of sensor units 301 included in the radiation detection apparatus 104. Any two adjacent sensor units 301 among the plurality of sensor units 301 included in the radiation detection apparatus 104 may have the configuration illustrated in FIG. 4.

The semiconductor layer 402 converts radiation into a charge. The top surface 401 of the semiconductor layer 402 is located on the side where the radiation 121 is incident. In the example in FIG. 4, the semiconductor layer 402 is located at an uppermost part of the sensor unit 301 (the location furthest from the frame 303). As such, the top surface of the semiconductor layer 402 constitutes the top surface 401 of the sensor unit 301.

The semiconductor layer 402 may be a single-crystal substrate formed from a semiconductor that directly converts radiation into a charge, such as cadmium zinc telluride (CdZnTe) or cadmium telluride (CdTe). The semiconductor layer 402 may be a single-crystal substrate formed from a semiconductor such as silicon (Si), lead iodide ($PbI_2$), mercury iodide ($HgI_2$), bismuth iodide ($BiI_3$), thallium bromide (TlBr), or the like.

The top surface 401 of the sensor unit 301 is covered by the substrate 305. The entire top surface 401 of the sensor unit 301 may be covered by the substrate 305, or only a part of the top surface 401 of the sensor unit 301 may be covered by the substrate 305.

The top surface 401 of the sensor unit 301 (the top surface of the semiconductor layer 402, in the example in FIG. 4) and the bottom surface of a substrate 305 (the bottom surface of a conductive layer 412, in the example in FIG. 4) may be coupled to each other. This coupling may be achieved, for example, using a bonding agent or an adhesive. Variation in the heights of the top surfaces 401 of the plurality of sensor units 301 can be suppressed by coupling each of the plurality of sensor units 301 to the substrate 305 provided in common for the plurality of sensor units 301.

The substrate 305 may include an insulating layer 411 and the conductive layer 412. The substrate 305 may also be formed from a thin film or the like. The conductive layer 412 faces the top surface 401 of the sensor unit 301. The conductive layer 412 may be in contact with the top surface 401 of the sensor unit 301. The conductive layer 412 may be formed from a metal such as gold, silver, copper, or aluminum, an alloy, or the like, for example. The insulating layer 411 covers the conductive layer 412. The insulating layer 411 may be formed from, for example, carbon-fiber-reinforced plastic (CFRP), amorphous carbon, polyimide film, or the like.

The conductive layer 412 may be used to apply a voltage to the semiconductor layer 402. When used in this manner, the conductive layer 412 may be in contact with the semiconductor layer 402, or may be fixed to the semiconductor layer 402 using a conductive adhesive.

When the conductive layer 412 is used to apply a voltage to the semiconductor layer 402, each sensor unit 301 need not include a separate electrode for applying the voltage to the semiconductor layer 402, as illustrated in FIG. 4. However, each sensor unit 301 may include a separate electrode (not shown) for applying the voltage to the semiconductor layer 402. If each sensor unit 301 has a separate electrode, the substrate 305 need not include the conductive layer 412. When the conductive layer 412 is disposed in common for the semiconductor layers 402 of the plurality of sensor units 301 as in the example in FIG. 4, variation in the voltages supplied to each semiconductor layer 402 can be reduced.

Electrodes formed on the bottom surface of the semiconductor layer 402 and the electrodes formed on the top surface of the interposer 404 are electrically and physically connected to each other by bumps 403. Individual electrodes are formed on the bottom surface of the semiconductor layer 402 so as to correspond to pixels of the sensor unit 301. Electrodes formed on the bottom surface of the interposer 404 and the electrodes formed on the top surface of the integrated circuit 406 are electrically and physically connected to each other by bumps 405. The bumps 403 and 405 are formed from solder, for example. Anisotropic conductive films (ACFs) may be used instead of the bumps 403 and 405. The interposer 404 relays signals between the semiconductor layer 402 and the integrated circuit 406. The interposer 404 may be omitted.

The integrated circuit 406 is attached to the mounting board 407. The integrated circuit 406 may be an energy dispersive counting circuit (ERCE). For example, the integrated circuit 406 may have a function for counting electrical pulses produced when radiation photons are incident on the semiconductor layer 402. Instead, however, the integrated circuit 406 may read out a voltage according to the charge accumulated in the semiconductor layer 402 from the semiconductor layer 402.

Two sensor units 301 adjacent to each other in the array among the plurality of sensor units 301 are coupled to each other by a coupling member 410. As will be described later, the coupling member 410 is formed by vapor deposition. In other words, the coupling member 410 is formed from a material capable of being used as a vapor deposition material. An example of such a material will be described later. By forming the coupling member 410 by vapor deposition, the sensor units 301 can be more firmly coupled to each other, even when the coupling member 410 is thin, than when the coupling member 410 is formed from an adhesive or the like. As such, the gap between the two adjacent sensor units 301 (in particular, the gap between the two adjacent semiconductor layers 402) can be reduced. In addition, coupling the two adjacent sensor units 301 to each other makes it easier to maintain a state in which the gaps between these sensor units 301 are reduced. When the gap between the two adjacent sensor units 301 is large, the gap between the adjacent semiconductor layers 402 is also large, which increases the amount of radiation that cannot be detected. Reducing the gap between the two adjacent sensor units 301 as per the configuration illustrated in FIG. 4 enables highly-precise radiation detection, which improves the image quality of the radiological image. Furthermore, forming the coupling member 410 by vapor deposition makes it possible to reduce stress on the sensor units 301 (and on the semiconductor layers 402 in particular) more than when the coupling member 410 is formed from an adhesive or the like. An adhesive produces residual stress on the sensor units 301 due to the volume thereof decreasing during solidification, but vapor deposition does not produce such residual stress.

In the configuration illustrated in FIG. 4, the part of the coupling member 410 located between the two semiconductor layers 402 may have a thickness not greater than the pitch of the pixels formed in the sensor unit 301. When the coupling member 410 is insulative, the coupling member 410 can suppress electrical shorting between the semiconductor layer 402 of one of the sensor units 301 with the semiconductor layer 402 of another of the sensor units 301.

In the configuration illustrated in FIG. 4, the coupling member 410 couples the semiconductor layers 402 of two sensor units 301 adjacent to each other in the array with each other. The coupling member 410 also couples the interposers 404 of two sensor units 301 adjacent to each other in the array with each other. Furthermore, the coupling member 410 also couples the mounting boards 407 of two sensor units 301 adjacent to each other in the array with each other. The coupling member 410 fills the space between the two sensor units 301 adjacent to each other in the array, and may therefore be called a “filler”.

The coupling member 410 fills the space between the semiconductor layers 402 and the interposers 404 of the sensor units 301. This makes it possible to suppress shorting between the plurality of bumps 403. The coupling member 410 also fills the space between the interposers 404 and the mounting boards 407 of the sensor units 301. This makes it possible to suppress shorting between the plurality of bumps 405. The coupling member 410 covers the side surfaces of the semiconductor layer 402 and at least a part of the bottom surface of the semiconductor layer 402 in each of the sensor units 301. The coupling member 410 covers at least a part of the top surface of the interposer 404, the side surfaces of the interposer 404, and at least a part of the bottom surface of the interposer 404 in each of the sensor units 301. The coupling member 410 covers at least a part of the top surface of the mounting board 407 and the side surfaces of the mounting board 407 in each of the sensor units 301. The coupling member 410 covers the top surface of the substrate 305, the side surfaces of the substrate 305, and the parts of a base surface of the substrate 305 that do not face the sensor unit 301.

Figure 23:
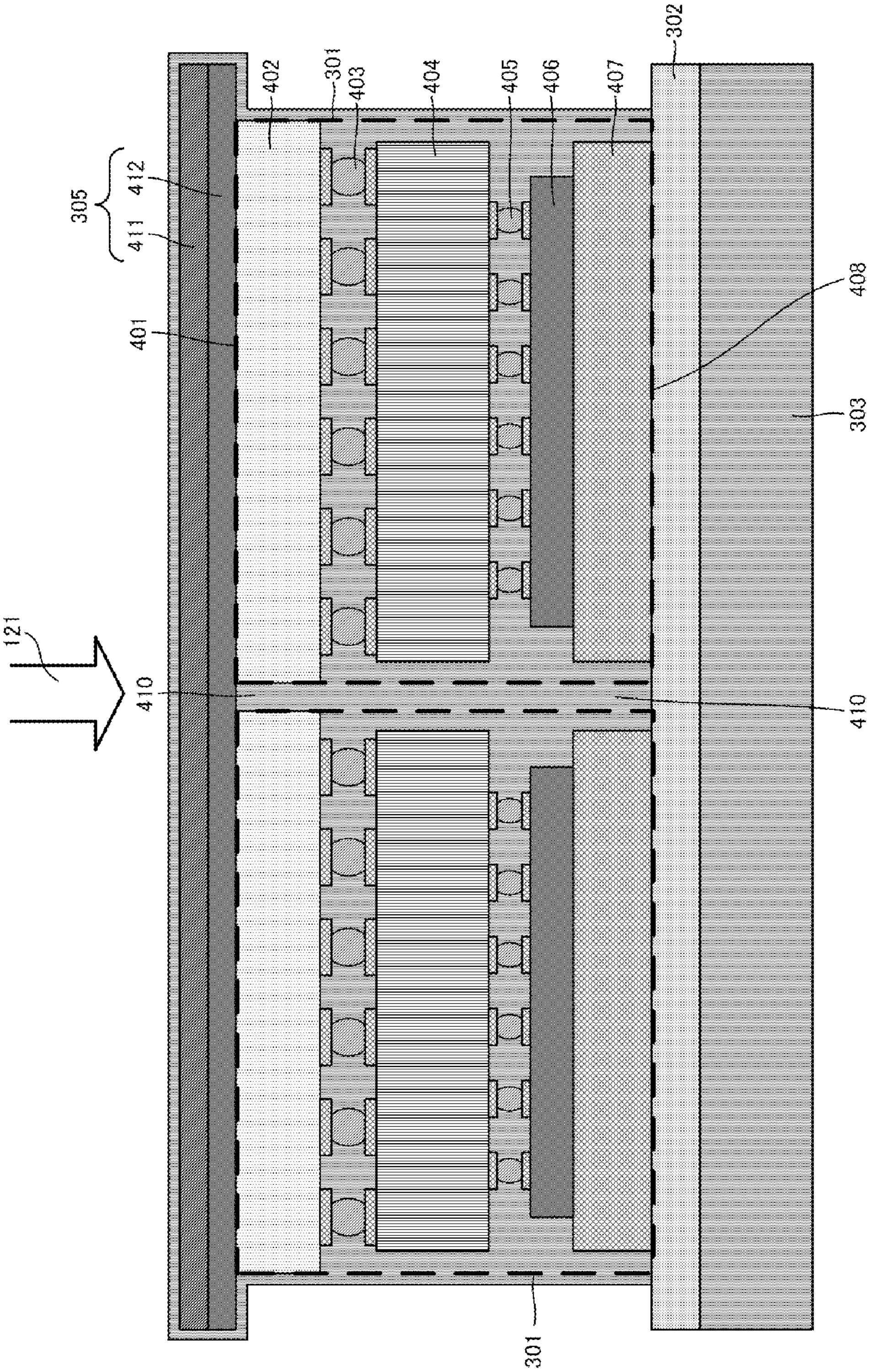
FIG. 23 is a cross-sectional view illustrating an example of the configuration of a sensor unit according to some embodiments.

As illustrated in FIG. 4, in plan view relative to the surface on which the radiation 121 is incident (the top surface of the substrate 305), the semiconductor layer 402 may be the same size as the mounting board 407 and the interposer 404. However, instead, as illustrated in FIG. 23, in plan view relative to the surface on which the radiation 121 is incident (the top surface of the substrate 305), the semiconductor layer 402 may be larger than the mounting board 407 and the interposer 404. This makes it easier to reduce the gap between the two adjacent semiconductor layers 402.

In the example in FIG. 4, the mounting board 407 is located at the lowermost part of the sensor unit 301 (the location closest to the frame 303). As such, the bottom surface of the mounting board 407 forms the bottom surface 408 of the sensor unit 301. The heat dissipation member 302 is located between the sensor unit 301 and the frame 303. The heat dissipation member 302 is in contact with the frame 303 and the bottom surface 408 of the sensor unit 301.

The functions of the heat dissipation member 302 will be described next. The thicknesses of the plurality of sensor units 301*a* to 301*d* (i.e., the distances between the top surfaces and the bottom surfaces) vary due to manufacturing error and the like. As such, attaching the plurality of sensor units 301*a* to 301*d* directly to the flat surface of the frame 303 may cause the heights of the semiconductor layers 402 (e.g., the distances from the frame 303) to vary. The heat dissipation member 302 may therefore be a member which is elastic so as to be capable of absorbing such variations.

When a single substrate 305 is used in common for the plurality of sensor modules 202, the substrate 305 can be curved in accordance with the shape of the base 201. In this case, the bottom surface of the substrate 305 may be a smooth curved surface. The bottom surface of the substrate 305 has a smooth surface at the parts in contact with the top surfaces 401 of the plurality of sensor units 301, and the other parts need not be smooth (e.g., may have an opening).

The substrate 305 may have a grid for reducing scattered rays. The number of components of the radiation detection apparatus 104 can be reduced by having the substrate 305 function both to align the sensor units 301 and reduce scattered rays.

A variation on the configuration of the radiation detection apparatus 104 illustrated in FIG. 4 will be described with reference to FIG. 5. The configuration illustrated in FIG. 5 differs from the configuration illustrated in FIG. 4 in terms of the shape of the coupling member 410. Other aspects of the configuration illustrated in FIG. 5 may be the same as the configuration illustrated in FIG. 4. In the configuration illustrated in FIG. 5, the coupling member 410 does not fill the space between the semiconductor layers 402 and the interposers 404 of the sensor units 301. The coupling member 410 also does not fill the space between the interposers 404 and the mounting boards 407 of the sensor units 301. Furthermore, the top surface of the substrate 305 and the side surfaces of the substrate 305 are not covered by the coupling member 410.

Figure 5:
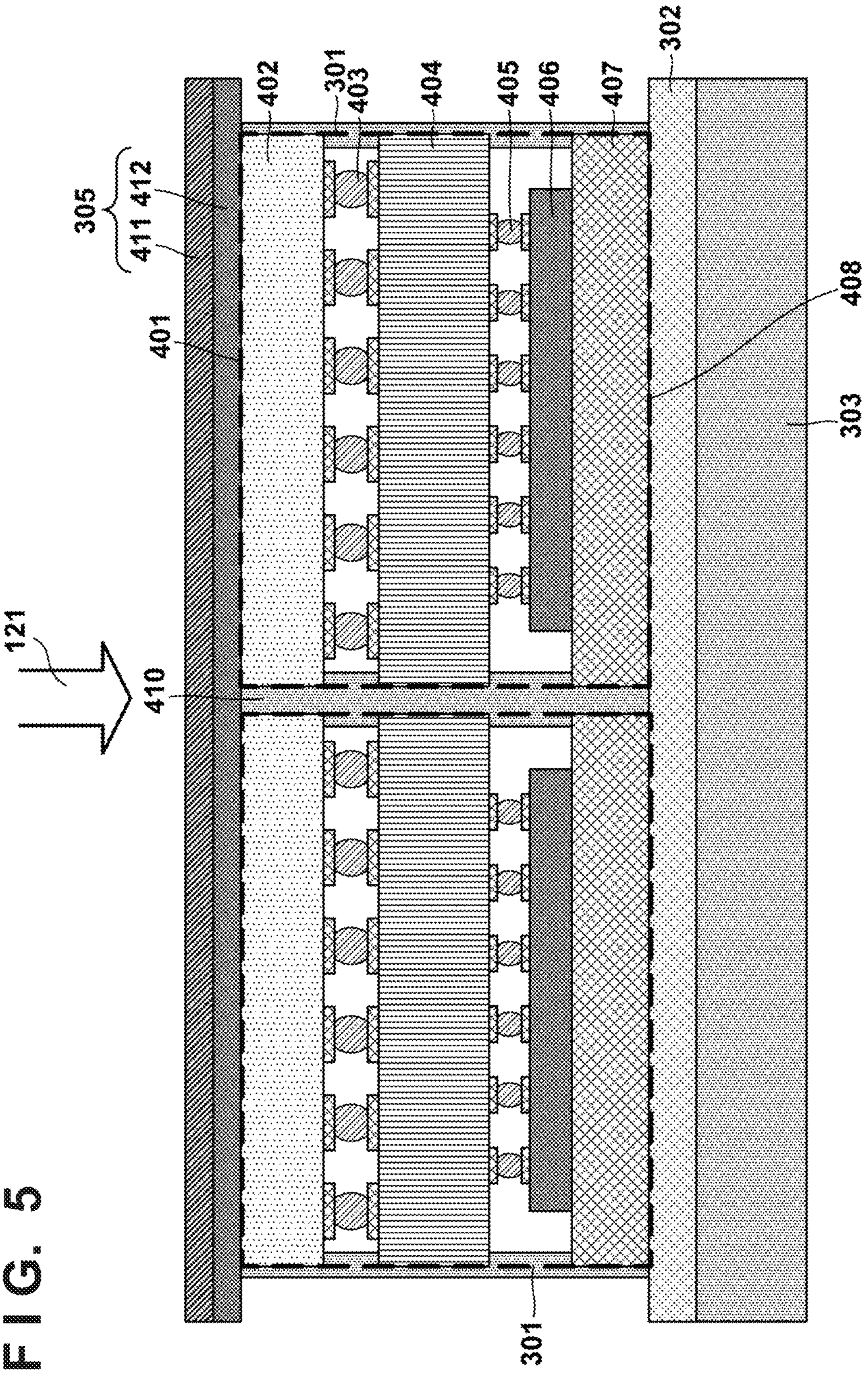
FIG. 5 is a cross-sectional view illustrating an example of the configuration of a sensor unit according to some embodiments.

Even with the configuration illustrated in FIG. 5, two sensor units 301 adjacent to each other in the array among the plurality of sensor units 301 are coupled to each other by the coupling member 410. Specifically, two adjacent semiconductor layers 402, two adjacent interposers 404, and two adjacent mounting boards 407 are coupled to each other by the coupling member 410.

Another variation on the configuration of the radiation detection apparatus 104 illustrated in FIG. 4 will be described with reference to FIG. 6. The configuration illustrated in FIG. 6 differs from the configuration illustrated in FIG. 4 in terms of the shape of the coupling member 410. Other aspects of the configuration illustrated in FIG. 6 may be the same as the configuration illustrated in FIG. 4. In the configuration illustrated in FIG. 6, the coupling member 410 does not fill the space between the semiconductor layers 402 and the interposers 404 of the sensor units 301. The coupling member 410 also does not fill the space between the interposers 404 and the mounting boards 407 of the sensor units 301. Furthermore, the top surface of the substrate 305 and the side surfaces of the substrate 305 are not covered by the coupling member 410.

Figure 6:
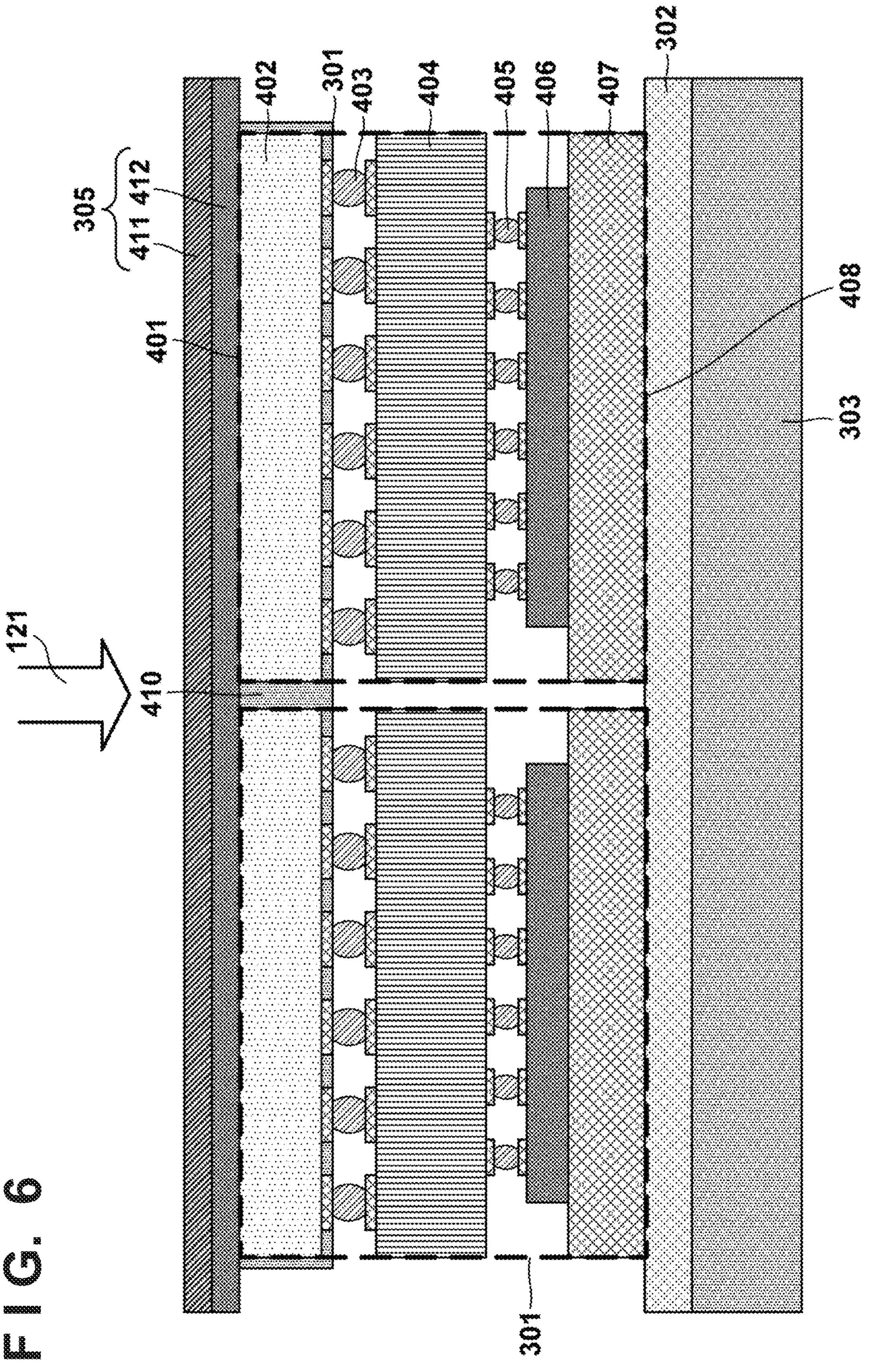
FIG. 6 is a cross-sectional view illustrating an example of the configuration of a sensor unit according to some embodiments.

Even with the configuration illustrated in FIG. 6, two sensor units 301 adjacent to each other in the array among the plurality of sensor units 301 are coupled to each other by the coupling member 410. Specifically, two adjacent semiconductor layers 402 are coupled to each other by the coupling member 410. However, the two adjacent interposers 404 and two adjacent mounting boards 407 are not coupled to each other by the coupling member 410. The coupling member 410 covers the side surfaces of the semiconductor layer 402 and at least a part of the bottom surface of the semiconductor layer 402 in each of the sensor units 301. The coupling member 410 is not in contact with the interposer 404 and the mounting board 407 in each of the sensor units 301.

Another variation on the configuration of the radiation detection apparatus 104 illustrated in FIG. 4 will be described with reference to FIG. 7. The configuration illustrated in FIG. 7 differs from the configuration illustrated in FIG. 4 in that one of the sensor units 301 includes a plurality of semiconductor layers 402. Other aspects of the configuration illustrated in FIG. 7 may be the same as the configuration illustrated in FIG. 4. The same changes as those illustrated in FIG. 7 may be made to the configurations illustrated in FIGS. 5 and 6.

The plurality of semiconductor layers 402 included in a single sensor unit 301 are disposed so as to form an array. The plurality of semiconductor layers 402 may form a one-dimensional array, or may form a two-dimensional array. Furthermore, a three-dimensional array may be formed by layering two or more semiconductor layers 402 in what is the vertical direction in the figure. Although the example illustrated in FIG. 7 illustrates two semiconductor layers 402 arranged side by side in one direction, three or more semiconductor layers 402 may be arranged side by side. The one sensor module 202 may have only one sensor unit 301 having a plurality of semiconductor layers 402 in this manner, or may have a plurality of sensor units 301 as per the configurations illustrated in FIGS. 4 to 6.

Figure 7:
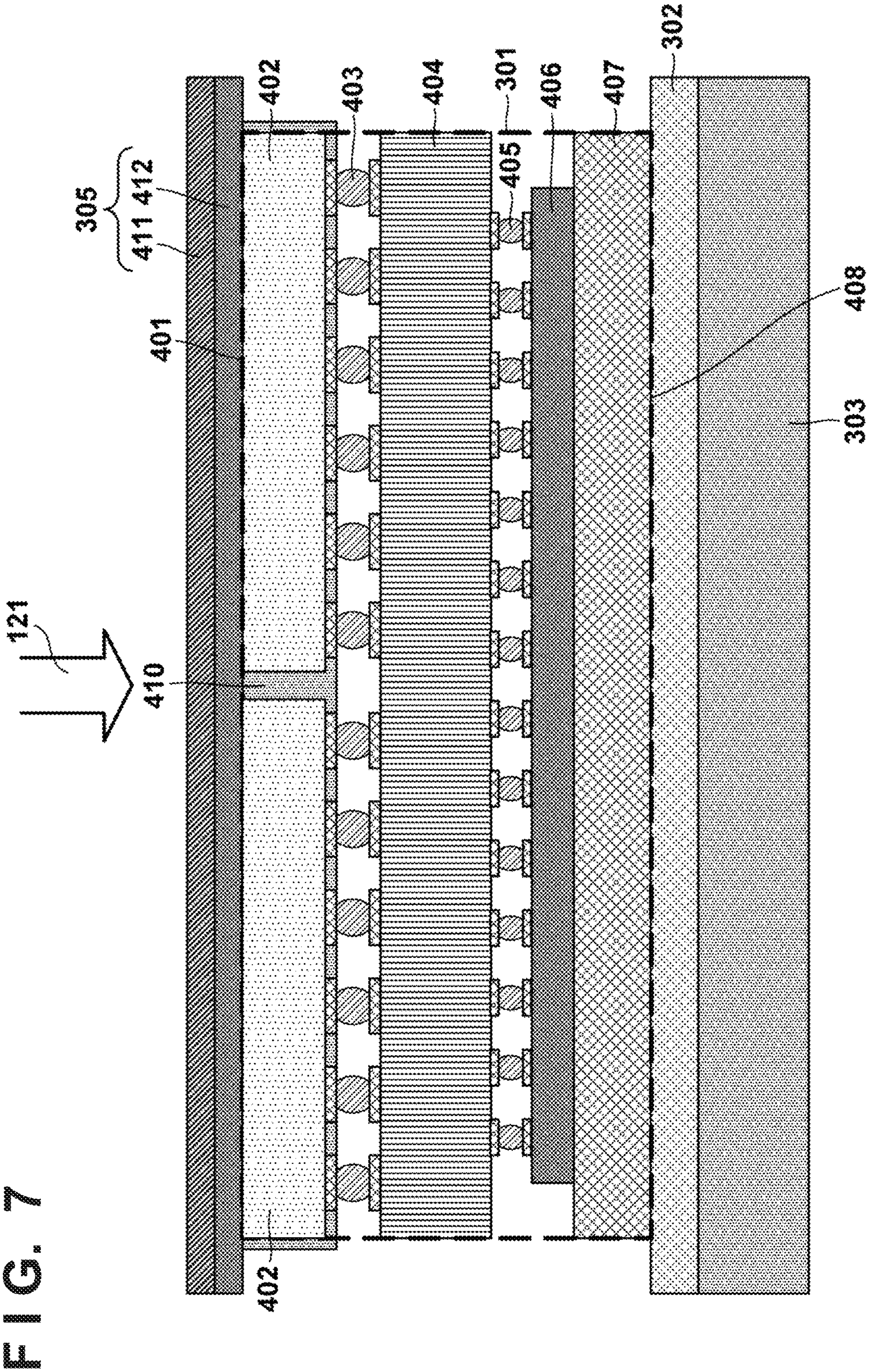
FIG. 7 is a cross-sectional view illustrating an example of the configuration of a sensor unit according to some embodiments.

In the configuration illustrated in FIG. 7, in the single sensor unit 301, a single interposer 404, a single integrated circuit 406, and a single mounting board 407 are disposed in common for the plurality of semiconductor layers 402. Instead, however, a plurality of at least one of the interposer 404, the integrated circuit 406, and the mounting board 407 may be disposed in a single sensor unit 301. Disposing the interposer 404, the integrated circuit 406, and the mounting board 407 together for the plurality of semiconductor layers 402 in a single sensor unit 301 makes it possible to simplify the process for mounting those elements. Additionally, collecting the cables (not shown) connecting the sensor unit 301 and the circuit board 304 makes it possible to reduce the number of cables, simplify the routing of the cables, and the like.

The two semiconductor layers 402 adjacent to each other in the array, among the plurality of semiconductor layers 402, are coupled by the coupling member 410. Similar to the configuration illustrated in FIG. 4, the coupling member 410 is formed by vapor deposition. The coupling member 410 covers the side surfaces of the semiconductor layer 402 and at least a part of the bottom surface of the semiconductor layer 402. The coupling member 410 is not in contact with the interposer 404 and the mounting board 407.

A variation on the configuration of the radiation detection apparatus 104 illustrated in FIG. 7 will be described with reference to FIG. 8. The configuration illustrated in FIG. 8 differs from the configuration illustrated in FIG. 7 in terms of the shape of the coupling member 410. Other aspects of the configuration illustrated in FIG. 8 may be the same as the configuration illustrated in FIG. 7. In the configuration illustrated in FIG. 8, the coupling member 410 is disposed only between the two adjacent semiconductor layers 402.

Figure 8:
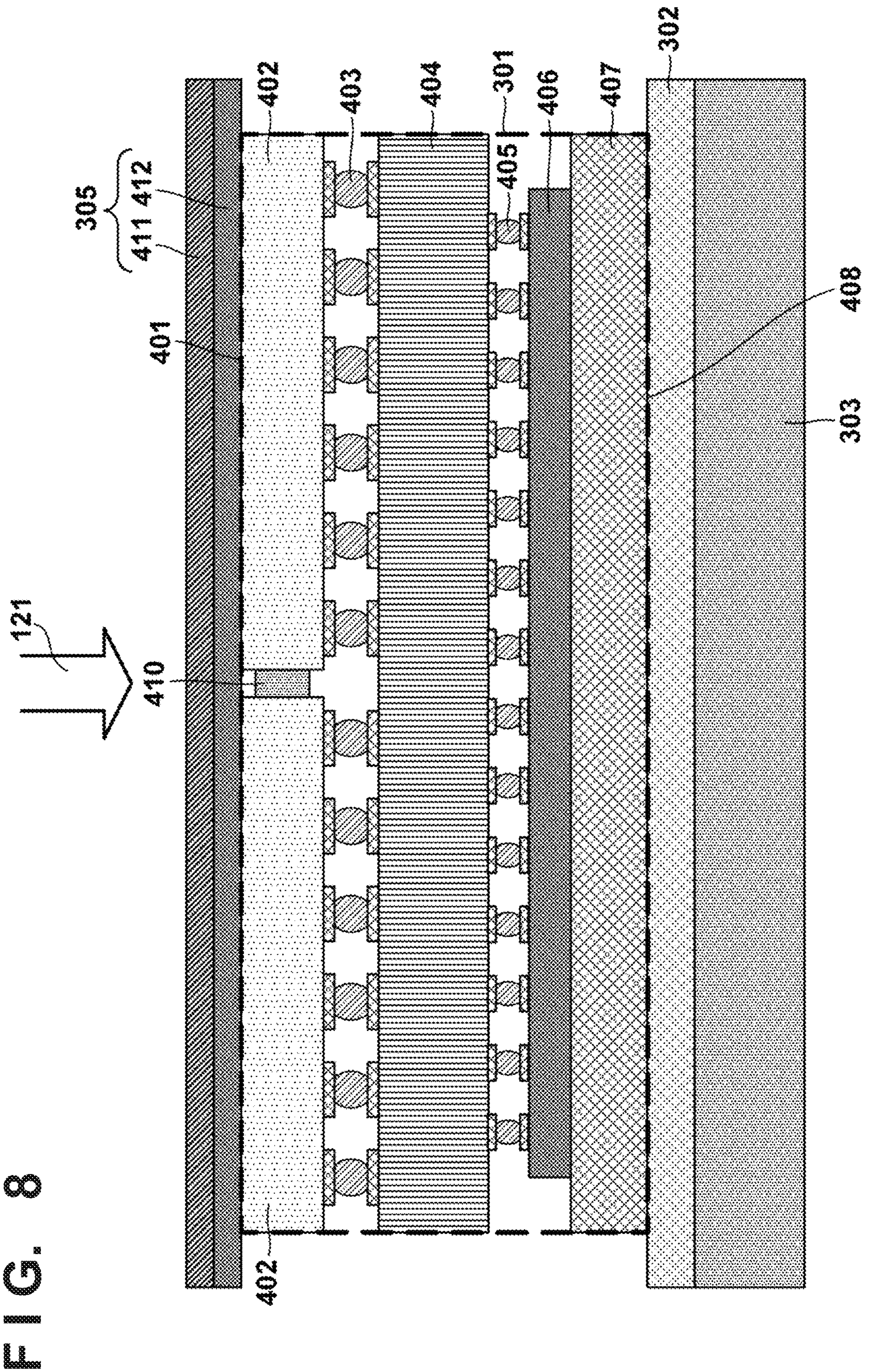
FIG. 8 is a cross-sectional view illustrating an example of the configuration of a sensor unit according to some embodiments.

Even with the configuration illustrated in FIG. 8, two sensor units 301 adjacent to each other in the array among the plurality of sensor units 301 are coupled to each other by the coupling member 410. Specifically, two adjacent semiconductor layers 402 are coupled to each other by the coupling member 410. The coupling member 410 partially covers the side surfaces of the semiconductor layer 402. The coupling member 410 is not in contact with the bottom surface of the semiconductor layer 402. The coupling member 410 is not in contact with the interposer 404 and the mounting board 407.

Figure 9:
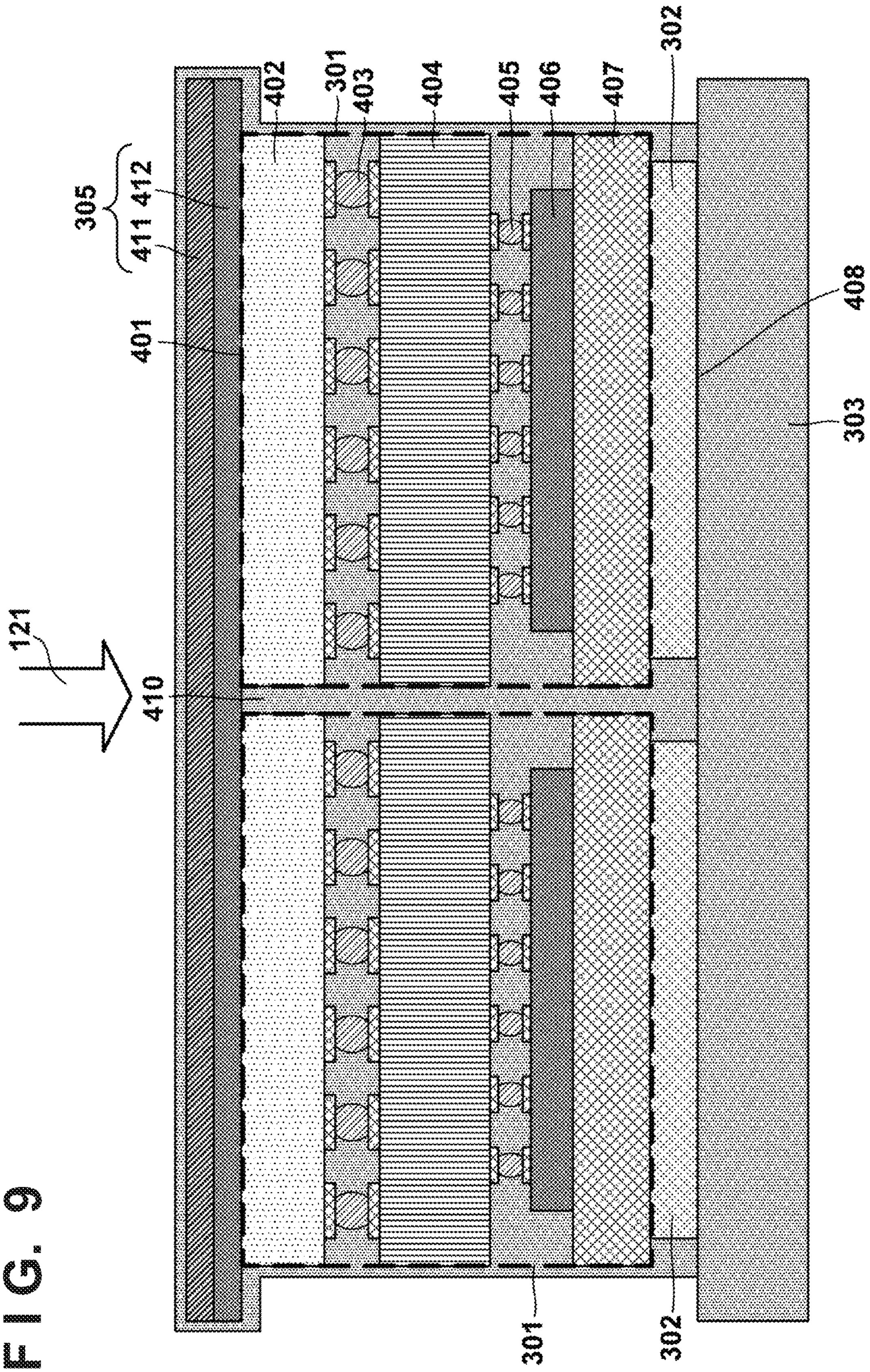
FIG. 9 is a cross-sectional view illustrating an example of the configuration of a sensor unit according to some embodiments.

Another variation on the configuration of the radiation detection apparatus 104 illustrated in FIG. 4 will be described with reference to FIG. 9. The configuration illustrated in FIG. 9 differs from the configuration illustrated in FIG. 4 in that the heat dissipation member 302 is provided individually for each of the sensor units 301. Other aspects of the configuration illustrated in FIG. 9 may be the same as the configuration illustrated in FIG. 4. The changes illustrated in FIG. 9 may be applied in the same manner to either of the configurations illustrated in FIGS. 5 and 6. The coupling member 410 covers the side surfaces of the heat dissipation member 302.

Figure 10A:
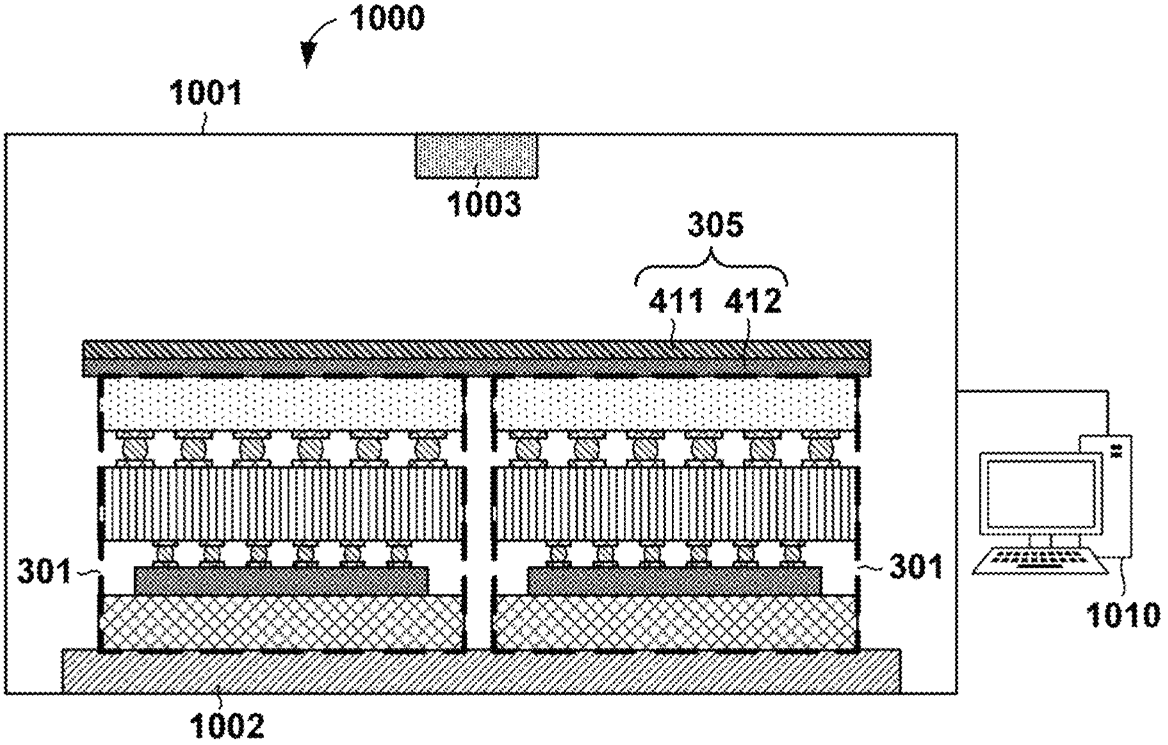
FIGS. 10A and 10B are cross-sectional views illustrating an example of a method for manufacturing a radiation detection apparatus according to some embodiments.

A method for manufacturing the radiation detection apparatus 104 according to some embodiments will be described with reference to FIGS. 10A to 12C. First, a method for manufacturing the radiation detection apparatus 104 illustrated in FIGS. 4 and 5 will be described with reference to FIGS. 10A and 10B. As illustrated in FIG. 10A, a plurality of the sensor units 301 are placed within a chamber 1001 of a vapor deposition device 1000. Each sensor unit 301 may include the components described with reference to FIG. 4. The sensor units 301 may be produced using an existing method, and thus the method for producing the sensor units 301 will not be described in detail here. The operations of the vapor deposition device 1000 are controlled by a control computer 1010. Specifically, the operations of the vapor deposition device 1000 are controlled by a processor of the control computer 1010 executing programs stored in a memory of the control computer 1010.

The plurality of sensor units 301 are disposed on a temporary fixing member 1002 so as to form an array. The substrate 305 is disposed on the plurality of sensor units 301. The substrate 305 may be coupled to each of the plurality of sensor units 301. The plurality of sensor units 301 may be fixed to the temporary fixing member 1002. The temporary fixing member 1002 may be an adhesive sheet, or may be an adsorption stage. Furthermore, the positions of the plurality of sensor units 301 relative to each other may be fixed by compressing the outer peripheries of the plurality of sensor units 301 inward. Disposing the plurality of sensor units 301 on the temporary fixing member 1002 makes the positions of the bottom surfaces of the plurality of sensor units 301 uniform. The temporary fixing member 1002 also functions as a mask during vapor deposition.

Figure 10B:
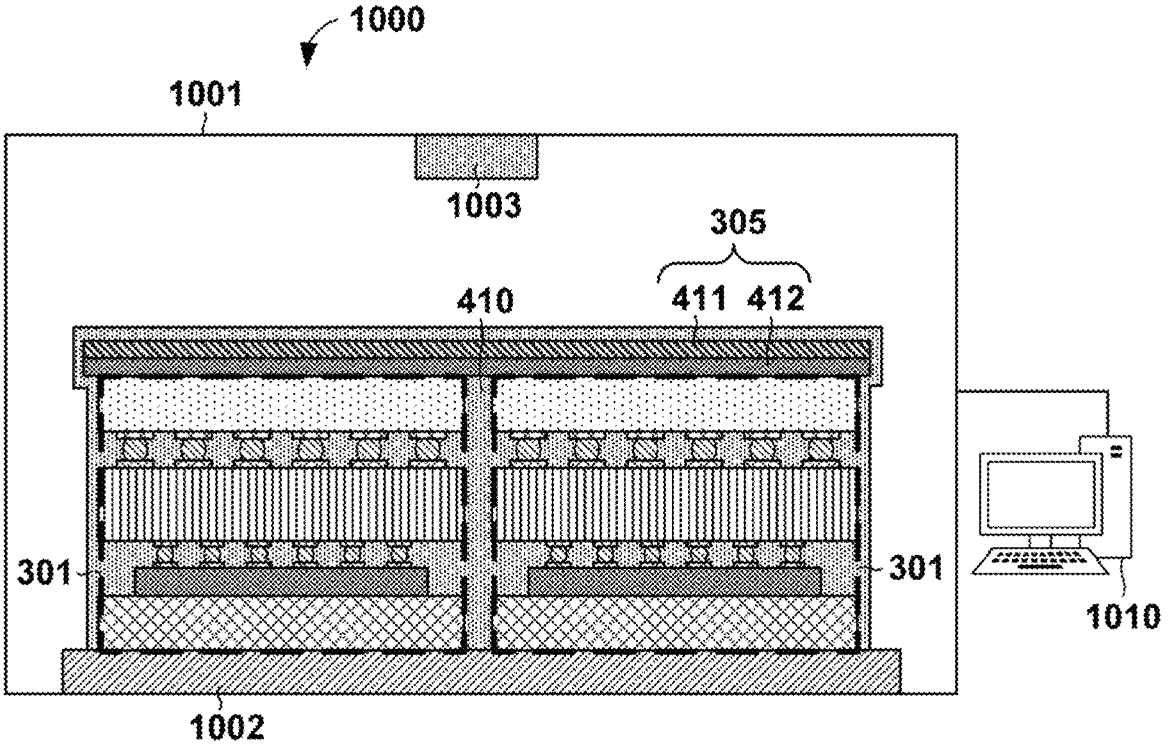

A vessel 1003 that holds vapor deposition material is also installed within the chamber 1001. As illustrated in FIG. 10B, the coupling member 410 is formed by vapor-depositing the vapor deposition material held in the vessel 1003 on the plurality of sensor units 301. As a result of this vapor deposition, the plurality of sensor units 301 are fixed to each other using the coupling member 410, forming an array. In the method illustrated in FIGS. 10A and 10B, the sensor units 301 are coupled to each other by the coupling member 410 with each sensor unit 301 being a unit structure. Specifically, the semiconductor layers 402, the interposers 404, and the mounting boards 407 of the two sensor units 301 adjacent to each other in the array are coupled to each other, respectively. The vapor deposition may be chemical deposition (e.g., chemical vapor deposition (CVD)), or physical deposition (e.g., physical vapor deposition (PVD)). The vapor deposition may be performed at normal temperature (e.g., a temperature in the range of 5° C. to 35° C.). Stress and distortion in the sensor unit 301 can be suppressed by performing the vapor deposition at normal temperature. In this manner, the plurality of unit structures included in the radiation detection apparatus 104 manufactured according to the method illustrated in FIGS. 10A and 10B are a plurality of the sensor units 301, and the radiation detection apparatus 104 includes a plurality of the sensor modules 202, each including a plurality of the sensor units 301.

An example of the vapor deposition material used for the vapor deposition will be described. The vapor deposition material may include one or more insulative organic materials, e.g., parylene, polyethylene, polytetrafluoroethylene, polyimide, polyamide, polyurea, and polyurethane. Parylene, polyimide, polyamide, polyurea, and polyurethane may be used in vapor deposition polymerization. Polyethylene and polytetrafluoroethylene may be used in physical vapor deposition. The coupling member 410 formed from such a material may be elastic. The elastic coupling member 410 may also function as a buffer material against heat, vibrations, and the like for the plurality of sensor units 301. Of these materials, parylene, for example, can be used for vapor deposition even when the work to be coated is at normal temperature.

The vapor deposition material may include one or more insulative inorganic materials, e.g., silicon oxide ($SiO_2$), aluminum oxide ($Al_2O_3$), and silicon nitride (SiN). These materials may be used in sputter deposition. The coupling member 410 formed from such a material may be rigid.

The vapor deposition material may include one or more insulative organic materials, e.g., TEOS (rational formula: $Si(OC_2H_5)_4$), TMB (rational formula: $B(OCH_3)_3$), TEB (rational formula: $B(OC_2H_5)_3$), TMP (rational formula: $P(OCH_3)_3$), TMOP (rational formula: $PO(OCH_3)_3$), TEOP (rational formula: $PO(OC_2H_5)_3$), TriMS (rational formula: $SiH(CH_3)_3$), and MTMS (rational formula: $CH_3Si(OCH_3)_3$). These materials may be used in chemical vapor deposition.

After the process illustrated in FIG. 10B, the plurality of sensor units 301 and the substrate 305 coupled to each other by the coupling member 410 are removed from the temporary fixing member 1002, and then removed from the chamber 1001 of the vapor deposition device 1000. Then, the plurality of sensor units 301 fixed to each other are attached to the frame 303 over the heat dissipation member 302. The sensor module 202 is produced as a result. Then, by attaching a plurality of the sensor modules 202 to the base 201, the radiation detection apparatus 104 illustrated in FIG. 4 is manufactured.

In the method illustrated in FIGS. 10A and 10B, the substrate 305 is attached to the plurality of sensor units 301 before the vapor deposition. Instead, however, the substrate 305 may be attached to the plurality of sensor units 301 after the vapor deposition (i.e., after forming the coupling member 410). The radiation detection apparatus 104 illustrated in FIG. 5 is manufactured as a result. If the vapor deposition is performed before the substrate 305 is attached to the plurality of sensor units 301, the top surface of each sensor unit 301 will be covered by the coupling member 410. The parts of the coupling member 410 covering the top surface of each sensor unit 301 may be removed before the substrate 305 is attached to the plurality of sensor units 301. This removal may be performed by separating a part of the coupling member 410, performing physical polishing or chemical polishing, or the like. Instead, however, the top surface of each sensor unit 301 may be covered with a mask member before the vapor deposition, and parts of the coupling member 410 may be removed along with the mask member after the vapor deposition.

Figure 11A:
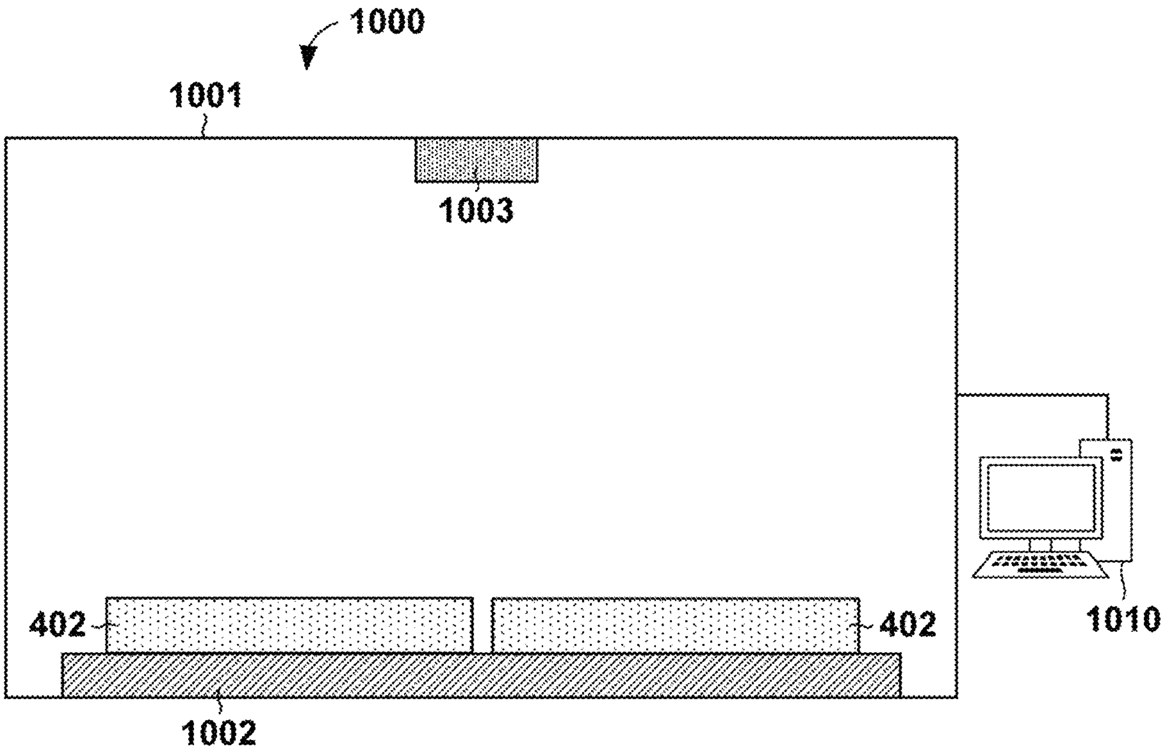
FIGS. 11A and 11B are cross-sectional views illustrating an example of a method for manufacturing a radiation detection apparatus according to some embodiments.

Next, a method for manufacturing the radiation detection apparatus 104 illustrated in FIGS. 6 to 8 will be described with reference to FIGS. 11A and 11B. Details that may be the same as in the manufacturing method illustrated in FIGS. 10A and 10B will be omitted. As illustrated in FIG. 11A, a plurality of the semiconductor layers 402 are placed within the chamber 1001 of the vapor deposition device 1000.

The plurality of semiconductor layers 402 are disposed on the temporary fixing member 1002 so as to form an array. The plurality of semiconductor layers 402 may be fixed to the temporary fixing member 1002. The positions of the plurality of semiconductor layers 402 relative to each other may be fixed by compressing the outer peripheries of the plurality of semiconductor layers 402 inward. Disposing the plurality of semiconductor layers 402 on the temporary fixing member 1002 makes the positions of the bottom surfaces of the plurality of semiconductor layers 402 uniform. The temporary fixing member 1002 also functions as a mask during vapor deposition.

The vessel 1003 that holds vapor deposition material is also installed within the chamber 1001. As illustrated in FIG. 11B, the coupling member 410 is formed by vapor-depositing the vapor deposition material held in the vessel 1003 on the plurality of semiconductor layers 402. As a result of this vapor deposition, the plurality of semiconductor layers 402 are fixed to each other using the coupling member 410, forming an array. In the method illustrated in FIGS. 11A and 11B, the semiconductor layers 402 are coupled to each other by the coupling member 410 with each semiconductor layer 402 being a unit structure. Specifically, two of the semiconductor layers 402 adjacent to each other in the array are coupled to each other. The vapor deposition material may be the same as the material used in the manufacturing method illustrated in FIGS. 10A and 10B.

Figure 11B:
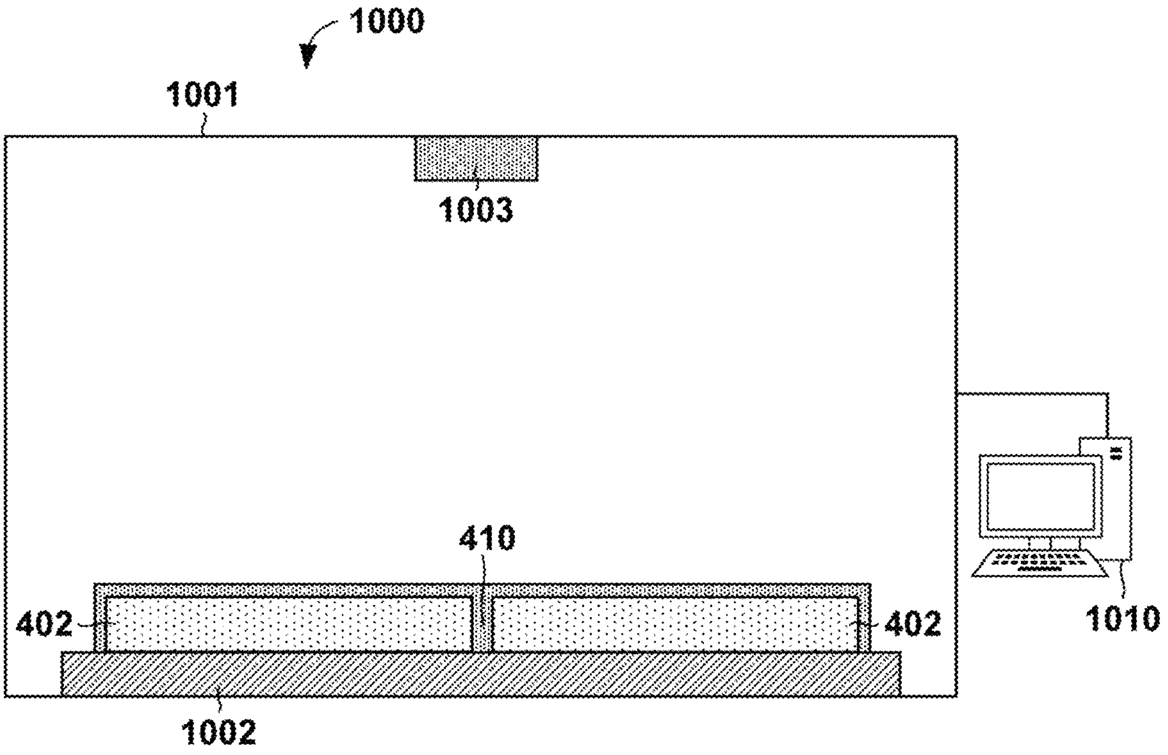

After the process illustrated in FIG. 11B, the plurality of semiconductor layers 402 coupled to each other by the coupling member 410 are removed from the temporary fixing member 1002, and then removed from the chamber 1001 of the vapor deposition device 1000. The plurality of semiconductor layers 402 fixed to each other are then coupled to the substrate 305. The parts of the coupling member 410 covering the top surface of each semiconductor layer 402 may be removed before coupling the plurality of semiconductor layers 402 to the substrate 305. This removal may be performed by separating a part of the coupling member 410, performing physical polishing or chemical polishing, or the like. Instead, however, the top surface of each semiconductor layer 402 may be covered with a mask member before the vapor deposition, and parts of the coupling member 410 may be removed along with the mask member after the vapor deposition.

The interposer 404 and the mounting board 407 are then formed. The interposer 404 and the mounting board 407 may be formed before the plurality of semiconductor layers 402 are coupled to the substrate 305. As illustrated in FIG. 6, the interposer 404 and the mounting board 407 may be formed for each of the semiconductor layers 402. The plurality of sensor units 301 are formed as a result. Instead, however, as illustrated in FIGS. 7 and 8, the interposer 404 and the mounting board 407 may be formed in common for the plurality of semiconductor layers 402. A single sensor unit 301 is formed as a result. Then, one or more sensor units 301 formed in this manner are attached to the frame 303 over the heat dissipation member 302. The sensor module 202 is produced as a result. Then, by attaching a plurality of the sensor modules 202 to the base 201, the radiation detection apparatus 104 illustrated in FIGS. 6 to 8 is manufactured.

In the method illustrated in FIGS. 11A and 11B, the substrate 305 is attached to the plurality of semiconductor layers 402 after the vapor deposition. Instead, however, the substrate 305 may be attached to the plurality of semiconductor layers 402 before the vapor deposition (i.e., before forming the coupling member 410).

Figure 12A:
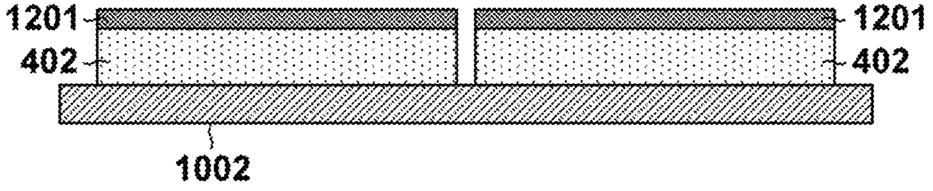
FIGS. 12A, 12B, and 12C are cross-sectional views illustrating an example of a method for manufacturing a radiation detection apparatus according to some embodiments.

A variation on the manufacturing method illustrated in FIGS. 11A and 11B will be described with reference to FIG. 12. The variation illustrated in FIG. 12 may be applied to the manufacturing method illustrated in FIGS. 10A and 10B. In the variation illustrated in FIG. 12A, a conductive layer 1201 is formed on the top surface of each semiconductor layer 402 before the vapor deposition. The plurality of semiconductor layers 402 and the plurality of conductive layers 1201 are then coupled to each other by the coupling member 410.

Figure 12B:
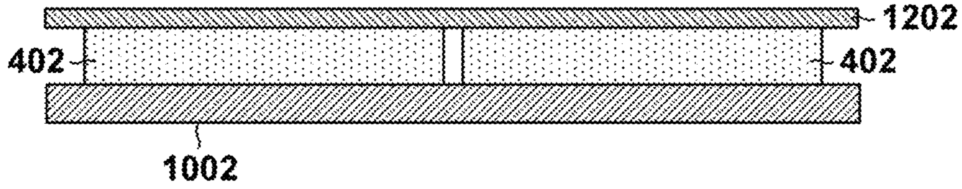

In the variation illustrated in FIG. 12B, the top surface of each semiconductor layer 402 is covered with a mask member 1202 before the vapor deposition. The plurality of semiconductor layers 402 are then coupled to each other by the coupling member 410. The mask member 1202 is then removed from the top surface of each semiconductor layer 402, which removes the coupling member 410 from the top surface of each semiconductor layer 402.

Figure 12C:
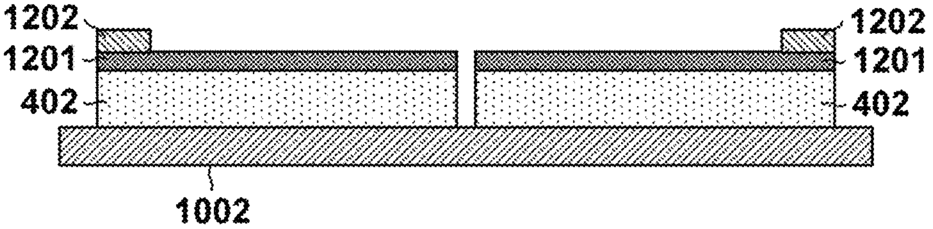

In the variation illustrated in FIG. 12C, the conductive layer 1201 is formed on the top surface of each semiconductor layer 402 before the vapor deposition. Furthermore, part of the top surface of the conductive layer 1201 is covered with the mask member 1202. The plurality of semiconductor layers 402 are then coupled to each other by the coupling member 410. The mask member 1202 is then removed from the top surface of each conductive layer 1201, which exposes part of the top surface of the conductive layer 1201. This part may be used to draw out the electrode.

Figure 13:
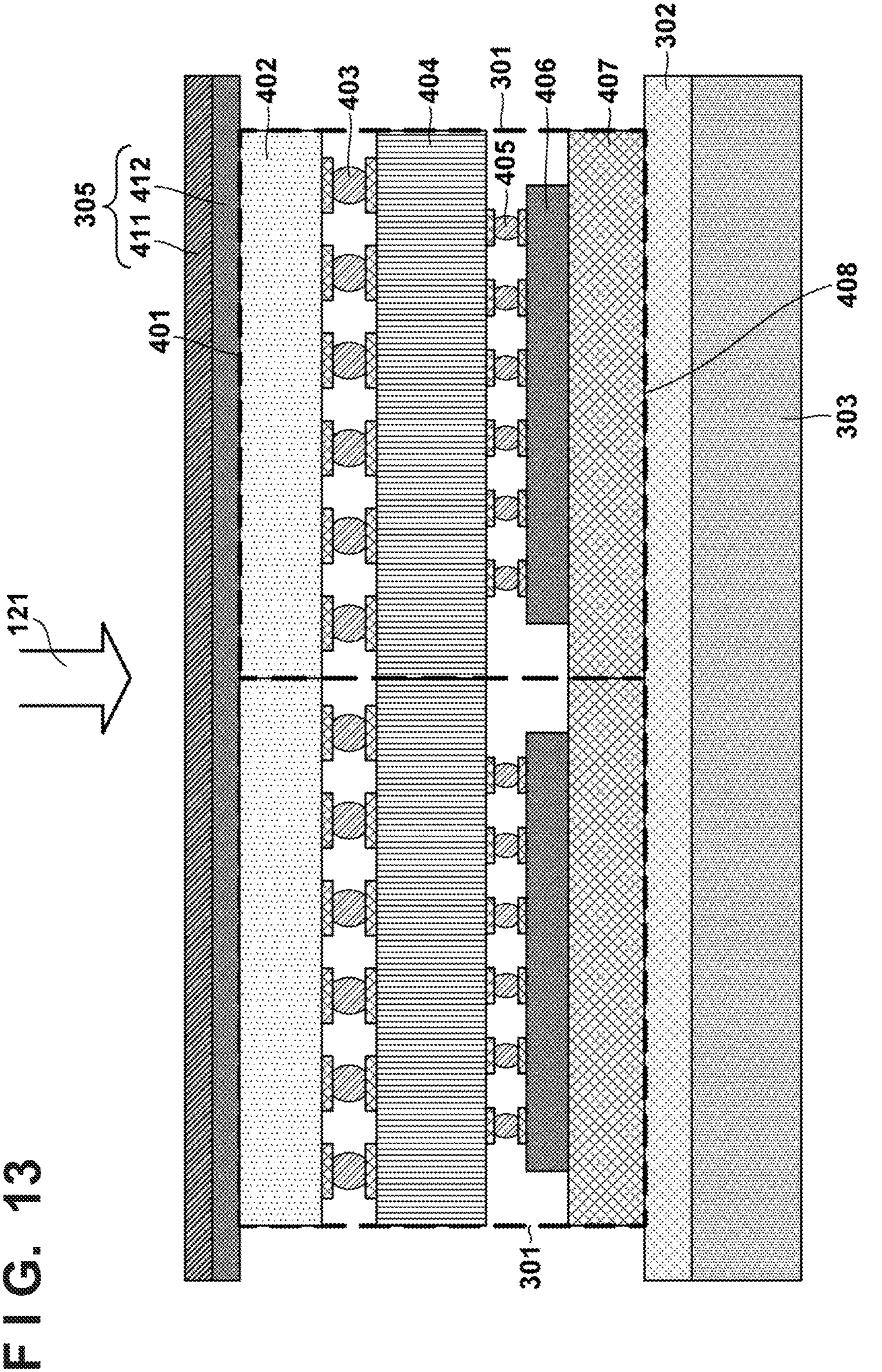
FIG. 13 is a cross-sectional view illustrating an example of the configuration of a sensor unit according to some embodiments.

Another example of the configuration of the sensor unit 301 will be described next with reference to the cross-sectional view in FIG. 13. Configurations that may be the same as those illustrated in FIG. 4 will not be described again. The top surface 401 of the sensor unit 301 (the top surface of the semiconductor layer 402, in the example in FIG. 13) and the bottom surface of the substrate 305 (the bottom surface of a conductive layer 412, in the example in FIG. 13) may be in contact with each other. The top surface 401 of the sensor unit 301 and the bottom surface of the substrate 305 may or may not be bonded to each other at a contact surface. When the top surface 401 of the sensor unit 301 and the bottom surface of the substrate 305 are bonded to each other, the bonding may be realized by solid-phase bonding, as will be described later. In this case, the sensor unit 301 (the semiconductor layer 402, in the example in FIG. 13) and the substrate 305 (the conductive layer 412, in the example in FIG. 13) are bonded by the cohesive force among the atoms.

Variation in the heights of the top surfaces 401 of the plurality of sensor units 301 can be suppressed by bringing each of the plurality of sensor units 301 into contact with the substrate 305 provided in common for the plurality of sensor units 301. Additionally, the state in which variation in the heights of the top surfaces 401 of the plurality of sensor units 301 is suppressed becomes easier to maintain by bonding each of the plurality of sensor units 301 to the substrate 305 provided in common for the plurality of sensor units 301. The height of the top surface 401 may be a height relative to the bottom surface of the substrate 305. If the heights of the top surfaces 401 vary, for example, radiation directed diagonally toward one sensor unit 301 may be detected by another sensor unit 301. Suppressing variation in the heights of the top surfaces 401 of the plurality of sensor units 301 enables highly-precise radiation detection, which improves the image quality of the radiological image.

Two of the sensor units 301 adjacent to each other in the array, among the plurality of sensor units 301, may be in contact with each other. For example, the semiconductor layers 402 of the two adjacent sensor units 301 may be in contact with each other. The interposers 404 of the two adjacent sensor units 301 may be in contact with each other. The mounting boards 407 of the two adjacent sensor units 301 may be in contact with each other. In the example in FIG. 13, all three of these members are in contact, but instead, only some of the three members may be in contact. The two adjacent sensor units 301 may or may not be bonded to each other at a contact surface. When the two adjacent sensor units 301 are bonded to each other, the bonding may be realized by solid-phase bonding, as will be described later. In this case, the two adjacent sensor units 301 are bonded to each other by the cohesive force between atoms.

Having the two adjacent sensor units 301 in contact with each other can reduce gaps between these sensor units 301. In addition, bonding the two adjacent sensor units 301 to each other makes it easier to maintain a state in which the gaps between these sensor units 301 are reduced. When the gap between the two adjacent sensor units 301 is large, the gap between the adjacent semiconductor layers 402 is also large, which increases the amount of radiation that cannot be detected. Reducing the gap between the two adjacent sensor units 301 as per the configuration illustrated in FIG. 13 enables highly-precise radiation detection, which improves the image quality of the radiological image.

The conductive layer 412 may be used to apply a voltage to the semiconductor layer 402. When used in this manner, the conductive layer 412 may be in contact with the semiconductor layer 402, and in particular, may be bonded thereto. When the conductive layer 412 and the semiconductor layer 402 are bonded to each other by solid-phase bonding (e.g., normal temperature bonding), the electrical resistance of the current path between the conductive layer 412 and the semiconductor layer 402 is lower than when a conductive adhesive is used for the coupling.

A variation on the configuration of the radiation detection apparatus 104 illustrated in FIG. 13 will be described with reference to FIG. 14. The configuration illustrated in FIG. 14 differs from the configuration illustrated in FIG. 13 in that an insulating layer 1401 is further provided between the two adjacent sensor units 301. Other aspects of the configuration illustrated in FIG. 14 may be the same as the configuration illustrated in FIG. 13.

Figure 14:
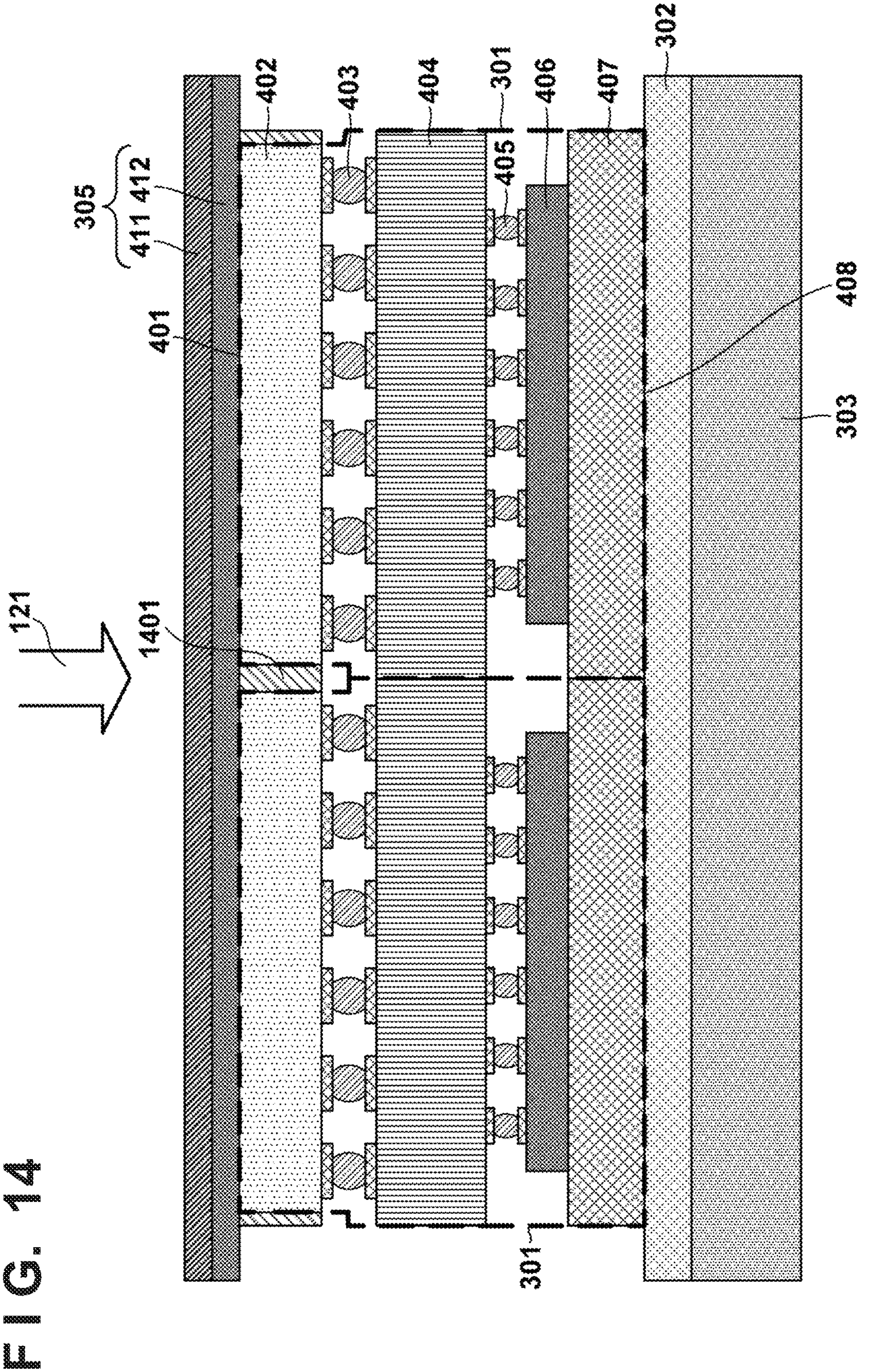
FIG. 14 is a cross-sectional view illustrating an example of the configuration of a sensor unit according to some embodiments.

As illustrated in FIG. 14, the insulating layer 1401 may be disposed between the semiconductor layers 402 of the two adjacent sensor units 301. Instead of or in addition thereto, the insulating layer 1401 may be disposed between the interposers 404 of the two adjacent sensor units 301. Instead of or in addition thereto, the insulating layer 1401 may be disposed between the mounting boards 407 of the two adjacent sensor units 301. In the configuration illustrated in FIG. 14, the insulating layer 1401 may have a thickness such that the gap between the two adjacent semiconductor layers 402 (i.e., the distance between the side surfaces thereof) is not greater than the pitch of the pixels formed in the sensor unit 301. The insulating layer 1401 can suppress electrical shorting between the semiconductor layer 402 of one of the sensor units 301 and the semiconductor layer 402 of another of the sensor units 301.

The sensor unit 301 (the semiconductor layer 402, in the example in FIG. 14) and the insulating layer 1401 may be in contact with each other. The sensor unit 301 and the insulating layer 1401 may or may not be bonded to each other at a contact surface. When the sensor unit 301 and the insulating layer 1401 are bonded to each other, the bonding may be realized by solid-phase bonding, as will be described later. In this case, the sensor unit 301 and the insulating layer 1401 are bonded to each other by the cohesive force between atoms. As illustrated in FIG. 14, the insulating layer 1401 may cover the entire side surface of the semiconductor layer 402. Instead, however, the insulating layer 1401 may only partially cover the side surface of the semiconductor layer 402.

The configuration illustrated in FIG. 14 is described as a configuration in which the insulating layer 1401 is not included in the sensor unit 301. Instead, however, each of the plurality of sensor units 301 may have an insulating layer, and the insulating layers of two adjacent sensor units 301 may be in contact with each other. The insulating layers may or may not be bonded to each other at a contact surface. When the insulating layers are bonded to each other, the bonding may be realized by solid-phase bonding, as will be described later.

Another variation on the configuration of the radiation detection apparatus 104 illustrated in FIG. 13 will be described with reference to FIG. 15. The configuration illustrated in FIG. 15 differs from the configuration illustrated in FIG. 13 in that one of the sensor units 301 includes a plurality of semiconductor layers 402. Other aspects of the configuration illustrated in FIG. 15 may be the same as the configuration illustrated in FIG. 13.

The plurality of semiconductor layers 402 included in a single sensor unit 301 are disposed so as to form an array. The plurality of semiconductor layers 402 may form a one-dimensional array, or may form a two-dimensional array. Furthermore, a three-dimensional array may be formed by layering two or more semiconductor layers 402 in what is the vertical direction in the figure. Although the example illustrated in FIG. 15 illustrates two semiconductor layers 402 arranged side by side in one direction, three or more semiconductor layers 402 may be arranged side by side. The one sensor module 202 may have only one sensor unit 301 having a plurality of semiconductor layers 402 in this manner, or may have a plurality of sensor units 301 as per the configurations illustrated in FIGS. 13 and 14.

Figure 15:
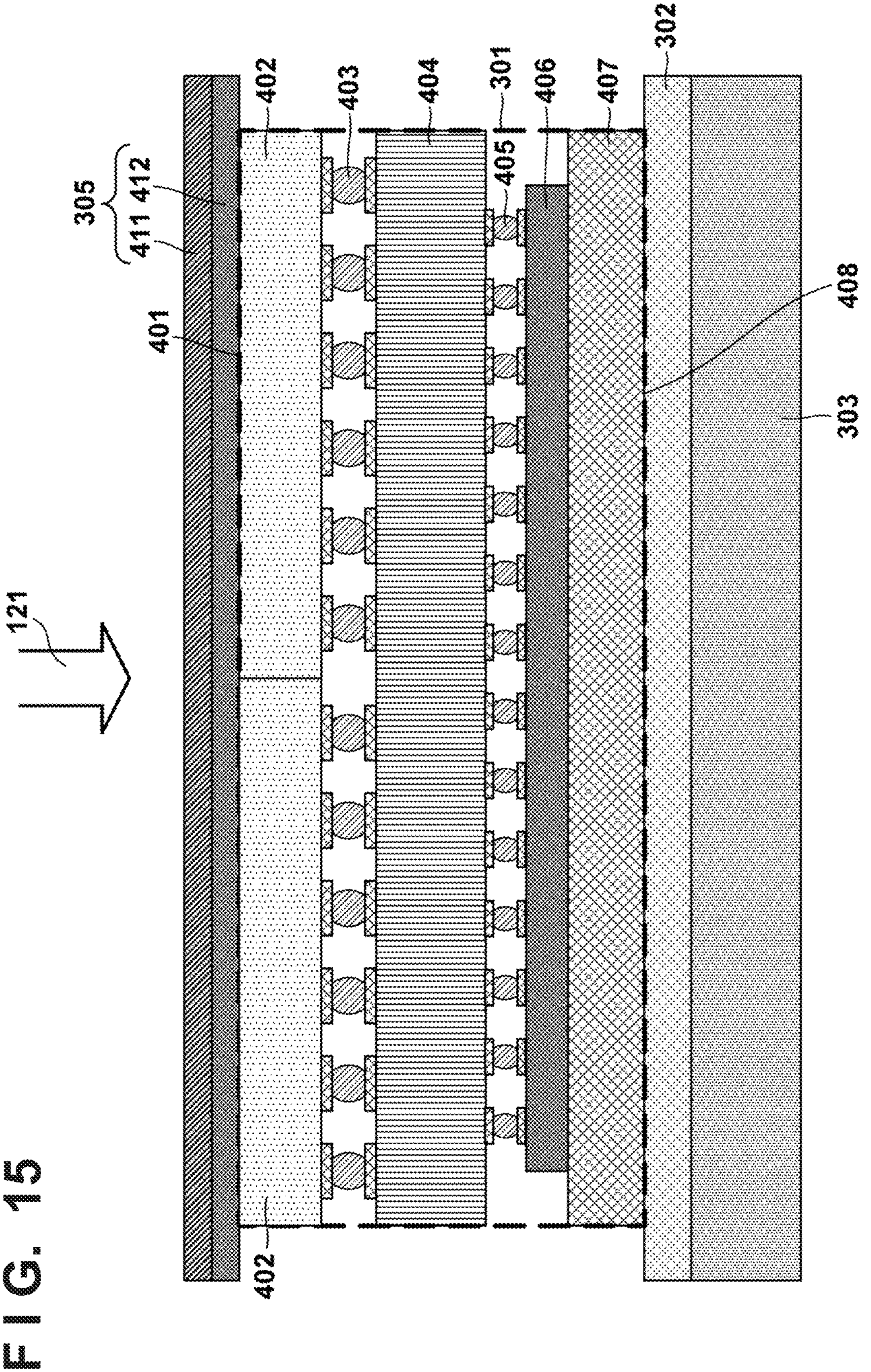
FIG. 15 is a cross-sectional view illustrating an example of the configuration of a sensor unit according to some embodiments.

In the configuration illustrated in FIG. 15, in the single sensor unit 301, a single interposer 404, a single integrated circuit 406, and a single mounting board 407 are disposed in common for the plurality of semiconductor layers 402. Instead, however, a plurality of at least one of the interposer 404, the integrated circuit 406, and the mounting board 407 may be disposed in a single sensor unit 301. Disposing the interposer 404, the integrated circuit 406, and the mounting board 407 together for the plurality of semiconductor layers 402 in a single sensor unit 301 makes it possible to simplify the process for mounting those elements. Additionally, collecting the cables (not shown) connecting the sensor unit 301 and the circuit board 304 makes it possible to reduce the number of cables, simplify the routing of the cables, and the like.

Two of the semiconductor layers 402 adjacent to each other in the array, among the plurality of semiconductor layers 402, may be in contact with each other. The two adjacent semiconductor layers 402 may or may not be bonded to each other at a contact surface. When the two adjacent semiconductor layers 402 are bonded to each other, the bonding may be realized by solid-phase bonding, as will be described later. In this case, the two adjacent semiconductor layers 402 are bonded to each other by the cohesive force between atoms.

In the configuration illustrated in FIG. 15, the two adjacent semiconductor layers 402 are in contact with each other. Instead, however, the radiation detection apparatus 104 may have an insulating layer between the two adjacent semiconductor layers 402, like the configuration illustrated in FIG. 14. Each of the two adjacent semiconductor layers 402 and the insulating layer may be in contact with each other, and may furthermore be bonded to each other. The bonding may be realized by solid-phase bonding.

A method for manufacturing the radiation detection apparatus 104 according to some embodiments will be described with reference to FIGS. 16A to 17C. As will be described later, solid-phase bonding is used in the method for manufacturing the radiation detection apparatus 104. Accordingly, solid-phase bonding will be described first with reference to FIGS. 16A to 17C.

Solid-phase bonding is a method in which two members are bonded to each other in a solid phase state (i.e., the members are not melted and instead remain solid) by pressurization, or by pressurization while being heated. Other methods of solid-phase bonding include fusion bonding (arc welding, laser welding, resistance welding), liquid-solid reactive bonding (brazing, liquid-phase diffusion bonding, thermal spraying, adhesion). Compared to these other methods, solid-phase bonding has the advantages that the members themselves do not reach high temperatures and do not dissolve; residual stress produced by differences in the thermal expansion coefficients of the members and the bonding material (wax, thermal spraying material, adhesive, or the like) is low; the crystalline state is less likely to change or weaken due to high temperatures; and the like. In particular, because there is no adhesive between the members, solid-phase bonding enables the gaps between the members to be made far narrower than in bonding using adhesive, which is commonly used.

Solid-phase bonding is performed by diffusing and rearranging the atoms of the two members. Solid-phase bonding can include two methods. One is a method in which two members are brought into contact with each other and bonded, and the other is a method in which two members are bonded using a metal inter-layer film. Both methods promote the movement of atoms at the bonding interface, which produces chemical bonds (metal bonds, in the case of metal materials). In particular, the metals are bonded to each other in a solid-phase state (below the melting point of the member) by the cohesive force between metal atoms acting on the metals in close proximity to each other. Solid-phase bonding methods include normal temperature bonding, solid-phase diffusion bonding, reactive diffusion bonding, hot pressure welding, cold pressure welding, ultrasonic welding, and the like. The following will describe a case where normal temperature bonding is used as an example of the solid-phase bonding. Normal temperature bonding is solid-phase bonding performed at normal temperature (e.g., between 5° C. and 35° C.). Instead, methods other than normal temperature bonding may be used in the solid-phase bonding.

Figure 16A:
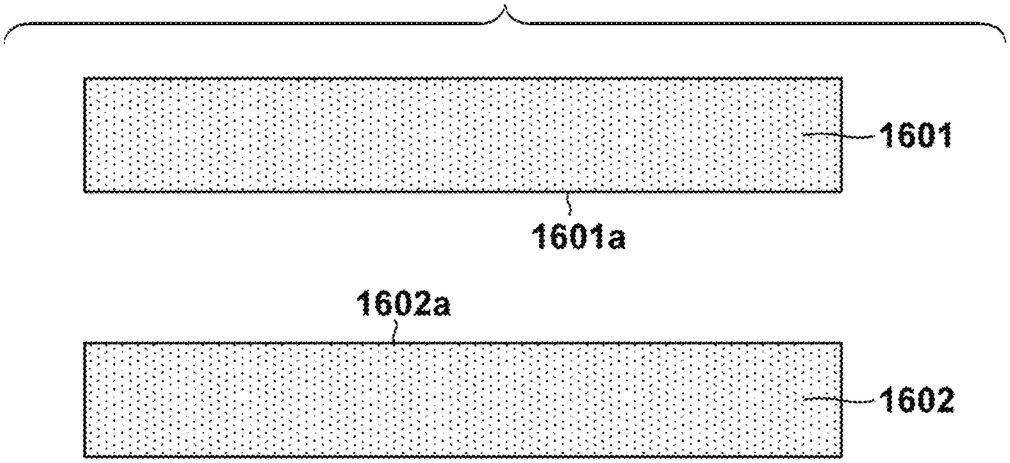
FIGS. 16A and 16B are cross-sectional views illustrating an example of solid-phase bonding in some embodiments.

A method for bringing two members into contact and bonding the members will be described with reference to FIGS. 16A and 16B. As illustrated in FIG. 16A, two members 1601 and 1602 to be bonded are prepared. The two members 1601 and 1602 may be formed from the same material, or may be formed from different materials. In this example, a face 1601*a* of the member 1601 and a face 1602*a* of the member 1602 are bonded.

First, the surfaces of the face 1601*a* and the face 1602*a* are treated. The following will describe the surface treatment for the face 1601*a*, but the same treatment may be carried out for the face 1602*a* as well. The surface treatment may include polishing the face 1601*a*. In this polishing, the face 1601*a* may be polished until the surface roughness of the face 1601*a* is not greater than Rmax=10 nm. The polishing may be performed through chemical mechanical polishing (CMP) or the like. A lower surface roughness of the face 1601*a* enables a lower contact pressure to be used in the bonding, and also makes it possible to increase the bonding strength. If the surface roughness of the face 1601*a* is low enough for normal temperature bonding before surface treatment, the face 1601*a* need not be polished. Furthermore, the surface treatment may include cleaning the inert layer of the face 1601*a* with an argon (Ar) beam or the like to activate the face 1601*a*. The face 1601*a* may be activated after polishing the face 1601*a*.

Figure 16B:
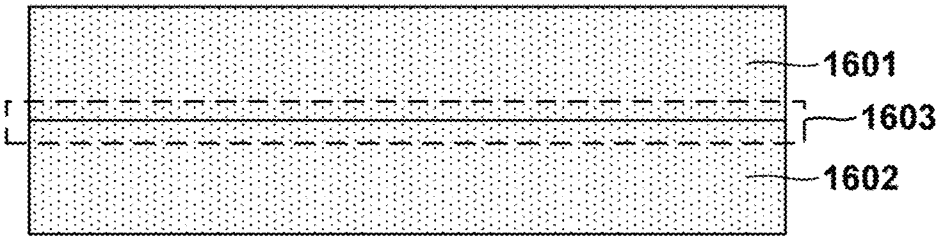

Then, the face 1601*a* and the face 1602*a* are brought into contact with each other, as illustrated in FIG. 16B. As a result, a cohesive force acts between the atoms in the member 1601 and the atoms in the member 1602 at an interface 1603 between the member 1601 and the member 1602. The member 1601 and the member 1602 are bonded to each other as a result. To suppress re-contamination of the surfaces in an activated state, the face 1601*a* and the face 1602*a* may be brought into contact under a high vacuum.

In solid-phase bonding, the entire parts of the face 1601*a* and the face 1602*a* in contact with each other may be bonded. Instead, however, in the solid-phase bonding, only part of the parts of the face 1601*a* and the face 1602*a* in contact with each other may be bonded, and the other parts may not be bonded. The unbonded parts may remain in the state from before the member 1601 and the member 1602 were bonded.

Figure 17A:
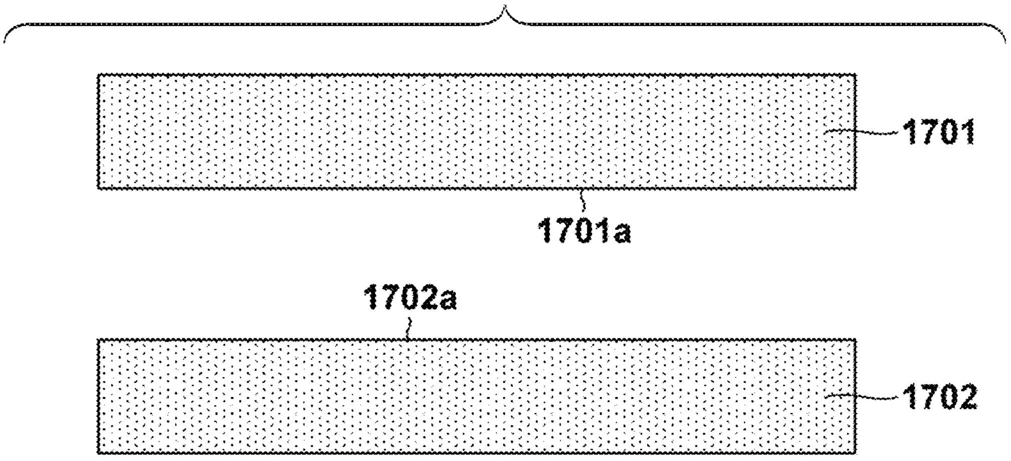
FIGS. 17A, 17B, and 17C are cross-sectional views illustrating an example of solid-phase bonding in some embodiments.

A method for bonding two members using a metal inter-layer film will be described with reference to FIGS. 17A to 17C. As illustrated in FIG. 17A, two members 1701 and 1702 to be bonded are prepared. The two members 1701 and 1702 may be formed from the same material, or may be formed from different materials. In this example, a face 1701*a* of the member 1701 and a face 1702*a* of the member 1702 are bonded.

First, the surfaces of the face 1701*a* and the face 1702*a* are treated. The following will describe the surface treatment for the face 1701*a*, but the same treatment may be carried out for the face 1702*a* as well. The surface treatment may include polishing the face 1701*a*. The polishing may be the same as the polishing described with reference to FIG. 16A.

Figure 17B:
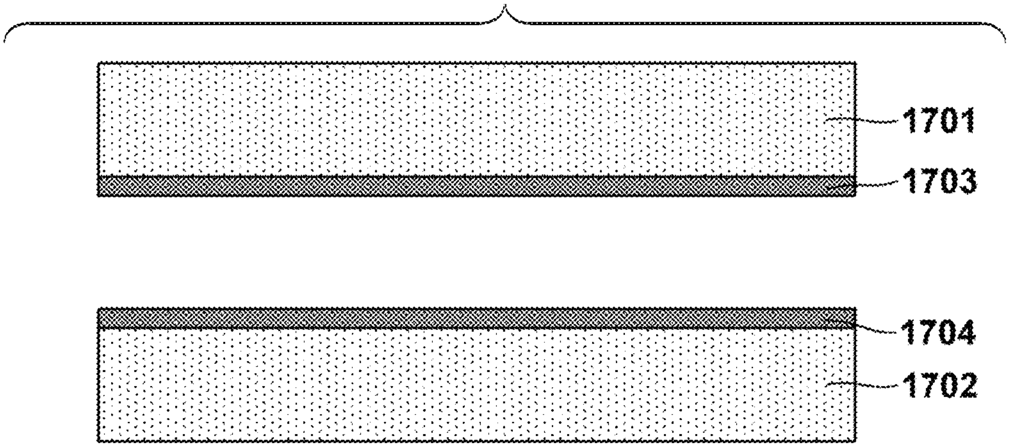

Then, as illustrated in FIG. 17B, a metal inter-laver film 1703 formed from gold (Au), silicon (Si), or the like is deposited on the face 1701*a* in a vacuum. To improve the adhesion of the metal inter-layer film 1703, another base layer, formed from titanium (Ti), for example, may be deposited onto the face 1701*a* before depositing the metal inter-layer film 1703.

Figure 17C:
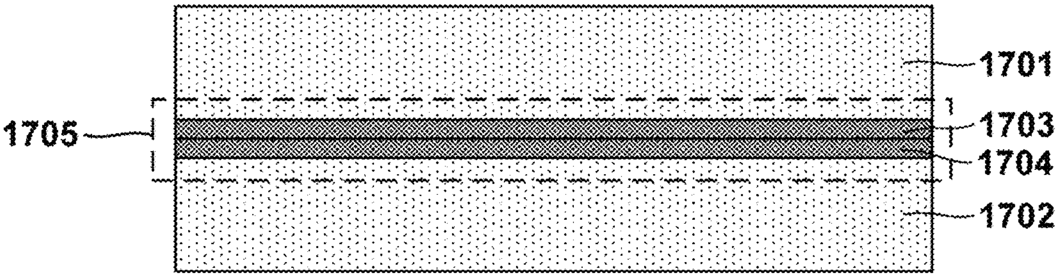

Then, as illustrated in FIG. 17C, the metal inter-layer film 1703 and a metal inter-layer film 1704 are brought into contact with each other. As a result, a cohesive force acts between the atoms in the metal inter-layer film 1703 and the atoms in the metal inter-layer film 1704 at an interface 1705 between the metal inter-layer film 1703 and the metal inter-layer film 1704. The member 1701 and the member 1702 are bonded to each other as a result. To suppress re-contamination of the surfaces in an activated state, the face 1701*a* and the face 1702*a* may be brought into contact under a high vacuum. The face 1701*a* and the face 1702*a* may be brought into contact at a low pressure. For example, the face 1701*a* and the face 1702*a* may be brought into contact at a pressure where the plastic deformation amount of the members 1701 and 1702 is not greater than 10%.

Figure 18A:
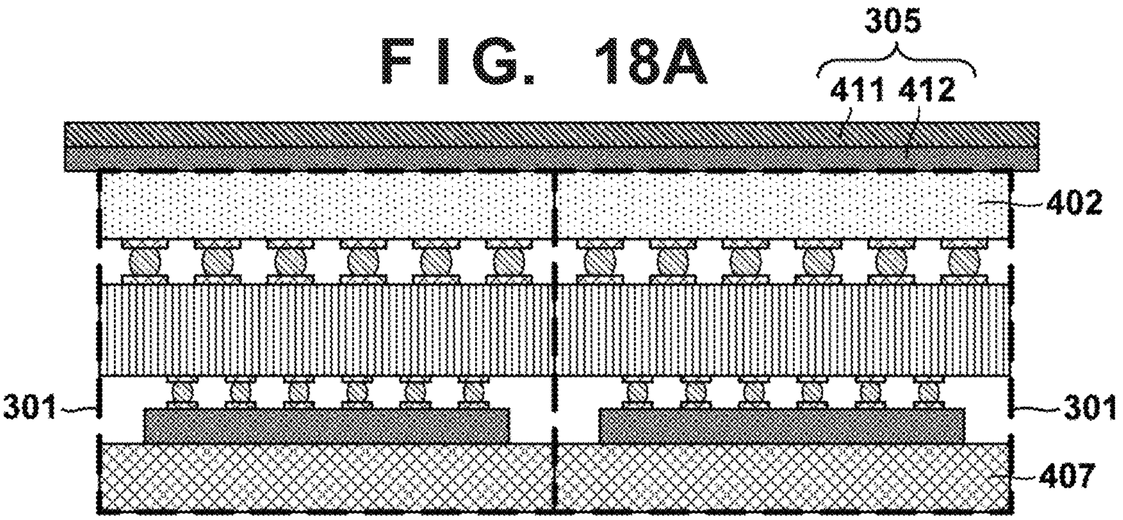
FIGS. 18A and 18B are cross-sectional views illustrating an example of a method for manufacturing a radiation detection apparatus according to some embodiments.

A method for manufacturing the radiation detection apparatus 104 according to some embodiments will be described with reference to FIGS. 18A and 18B. As illustrated in FIG. 18A, the substrate 305 and the plurality of sensor units 301 are prepared. The substrate 305 and the sensor units 301 may include the components described with reference to FIG. 13. The substrate 305 and the sensor units 301 may be produced using an existing method, and thus the method for producing the substrate 305 and the sensor units 301 will not be described in detail here.

The plurality of sensor units 301 are then fixed to each other to form an array by bonding each of the plurality of sensor units 301 and the substrate 305 to each other by using solid-phase bonding. As described above, the solid-phase bonding may be normal temperature bonding. The same applies to the solid-phase bonding described later with reference to FIGS. 19A to 21B. In the method illustrated in FIGS. 18A and 18B, the sensor units 301 are bonded to the substrate 305, with each sensor unit 301 being a unit structure. In this manner, the plurality of unit structures included in the radiation detection apparatus 104 manufactured according to the method illustrated in FIGS. 18A and 18B are a plurality of the sensor units 301, and the radiation detection apparatus 104 includes a plurality of the sensor modules 202, each including a plurality of the sensor units 301. The same applies to the radiation detection apparatus 104 manufactured according to the method illustrated in FIGS. 19A and 19B, described below.

The substrate 305 is provided in common for the plurality of sensor units 301. The substrate 305 includes the conductive layer 412 that is bonded to the plurality of sensor units 301, and an insulating layer 411 that is located on the opposite side of the plurality of sensor units 301 with respect to the conductive layer 412. Instead, however, the substrate 305 may have a different configuration, and need not include the conductive layer 412, for example.

Figure 18B:
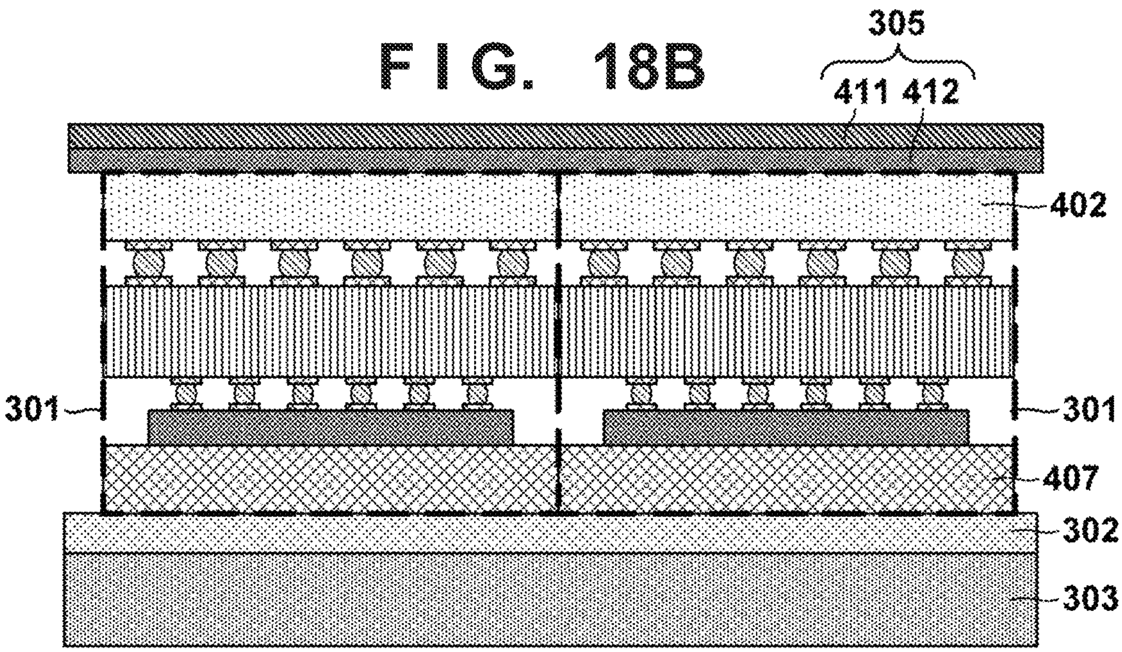

As illustrated in FIGS. 18A and 18B, the sensor unit 301 has the semiconductor layer 402 at the uppermost part thereof. As such, the semiconductor layer 402 in each of the plurality of sensor units 301 and the substrate 305 are bonded to each other by using solid-phase bonding. Instead, however, if the sensor unit 301 has a member other than the semiconductor layer 402 at the uppermost part thereof, that member and the substrate 305 are bonded to each other by using solid-phase bonding.

To suppress stress produced in the sensor unit 301, the solid-phase bonding between the plurality of sensor units 301 and the substrate 305 may be performed at a low pressure. For example, the solid-phase bonding may be performed at a pressure where the plastic deformation amount of the semiconductor layer 402 of the sensor unit 301 is not greater than 10%.

Two adjacent sensor units 301 among the plurality of sensor units 301 may or may not be in contact with each other, and may or may not be bonded to each other. Two adjacent sensor units 301 among the plurality of sensor units 301 may be bonded to each other by solid-phase bonding, or may be bonded by a method other than solid-phase bonding.

Then, as illustrated in FIG. 18B, the plurality of sensor units 301 fixed to each other are attached to the frame 303 over the heat dissipation member 302. The sensor module 202 is produced as a result. Then, by attaching a plurality of the sensor modules 202 to the base 201, the radiation detection apparatus 104 is manufactured.

Figure 19A:
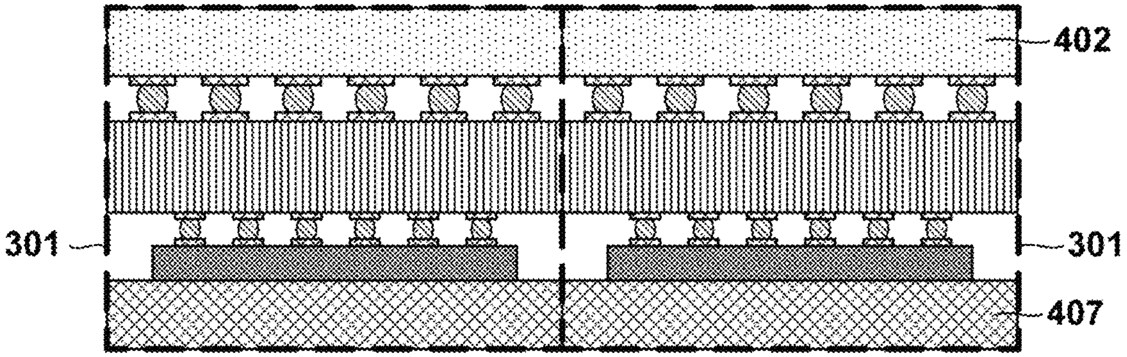
FIGS. 19A and 19B are cross-sectional views illustrating an example of a method for manufacturing a radiation detection apparatus according to some embodiments.

A method for manufacturing the radiation detection apparatus 104 according to another embodiment will be described with reference to FIGS. 19A and 19B. As illustrated in FIG. 19A, the plurality of sensor units 301 are prepared. Each sensor unit 301 may include the components described with reference to FIG. 13. The sensor units 301 may be produced using an existing method, and thus the method for producing the sensor units 301 will not be described in detail here.

Then, by bonding two sensor units 301 adjacent to each other in the array by using solid-phase bonding, the plurality of sensor units 301 are fixed to each other so as to form an array. In the method illustrated in FIGS. 19A and 19B, the sensor units 301 are bonded to the substrate 305, with each sensor unit 301 being a unit structure.

In the bonding between the sensor units 301, the semiconductor layers 402 of the two adjacent sensor units 301 may be bonded to each other by solid-phase bonding. Instead of or in addition thereto, the interposers 404 of the two adjacent sensor units 301 may be bonded to each other by solid-phase bonding. Instead of or in addition thereto, the mounting boards 407 of the two adjacent sensor units 301 may be bonded to each other by solid-phase bonding.

To suppress stress produced in the sensor unit 301, the solid-phase bonding between the two adjacent sensor units may be performed at a low pressure. For example, the solid-phase bonding may be performed at a pressure where the plastic deformation amount of the semiconductor layer 402 of the sensor unit 301 is not greater than 10%.

Figure 19B:
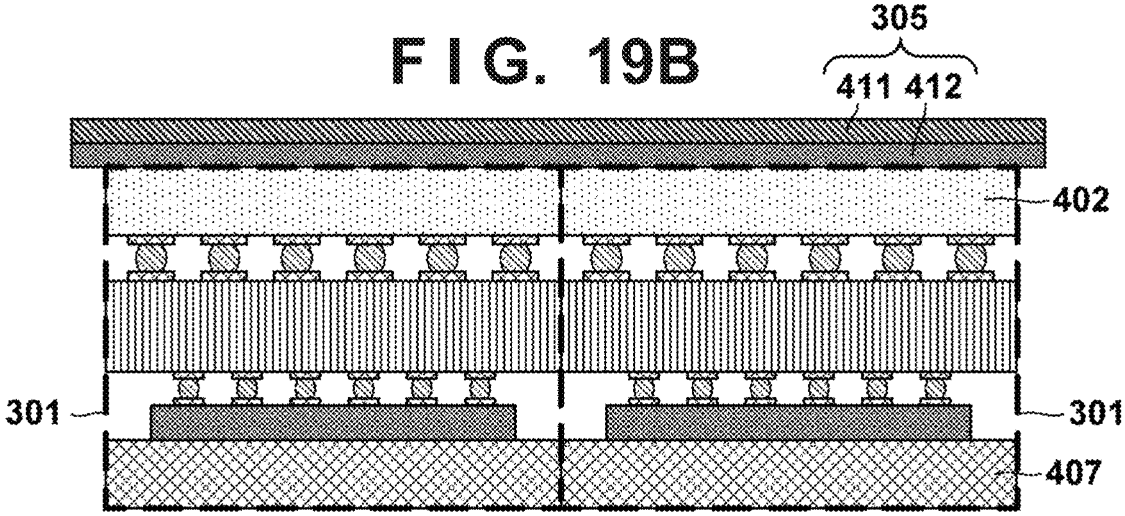

Then, as illustrated in FIG. 19B, the substrate 305 is prepared. The substrate 305 may include the components described with reference to FIG. 13. The substrate 305 may be produced using an existing method, and thus the method for producing the substrate 305 will not be described in detail here. The substrate 305 and the plurality of sensor units 301 are then bonded to each other. This bonding may be performed by solid-phase bonding, or by a method other than solid-phase bonding (fusion bonding, liquid-solid reactive bonding, or the like). In the method illustrated in FIGS. 19A and 19B, the plurality of sensor units 301 are bonded to each other in the process illustrated in FIG. 19A, and thus the substrate 305 and the plurality of sensor units 301 need not be bonded to each other, and may simply be in contact with each other. Instead, however, the radiation detection apparatus 104 need not include the substrate 305. Thereafter, the radiation detection apparatus 104 is manufactured by performing the steps described above with reference to FIG. 18B.

Figure 20A:
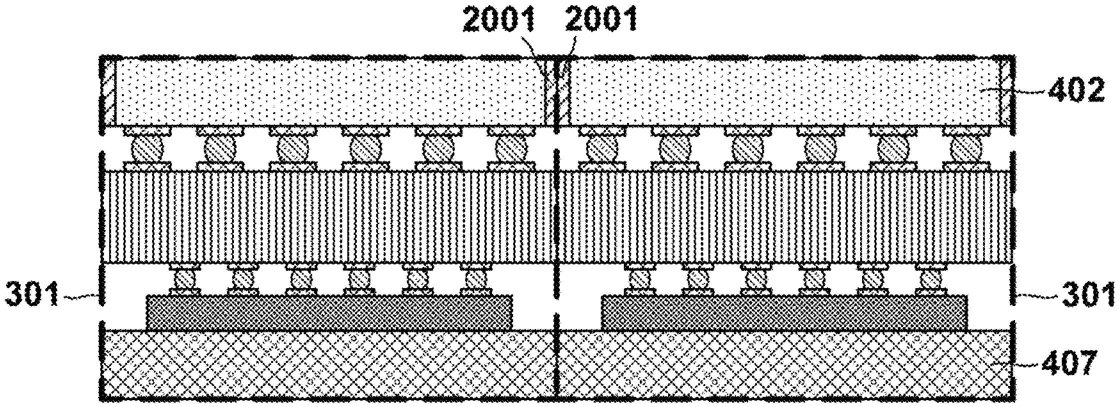
FIGS. 20A and 20B are cross-sectional views illustrating an example of a method for manufacturing a radiation detection apparatus according to some embodiments.

A method for manufacturing the radiation detection apparatus 104 according to another embodiment will be described with reference to FIG. 20A. Differences from the manufacturing method described with reference to FIGS. 19A and 19B will be described hereinafter. In the manufacturing method illustrated in FIG. 20A, each of the plurality of sensor units 301 has an insulating layer 2001. The insulating layer 2001 covers at least a part of the side surfaces of the semiconductor layer 402. The insulating layer 2001 may be bonded to the semiconductor layer 402 by solid-phase bonding, or may be formed on the semiconductor layer 402 by another method (e.g., sputtering). Then, in the bonding between the sensor units 301, the insulating layers 2001 of the two adjacent sensor units 301 may be bonded to each other by solid-phase bonding. The insulating layer 2001 may be formed from silicon dioxide, for example. In the manufacturing method illustrated in FIG. 20A, another member may be used instead of the insulating layer 2001.

Figure 20B:
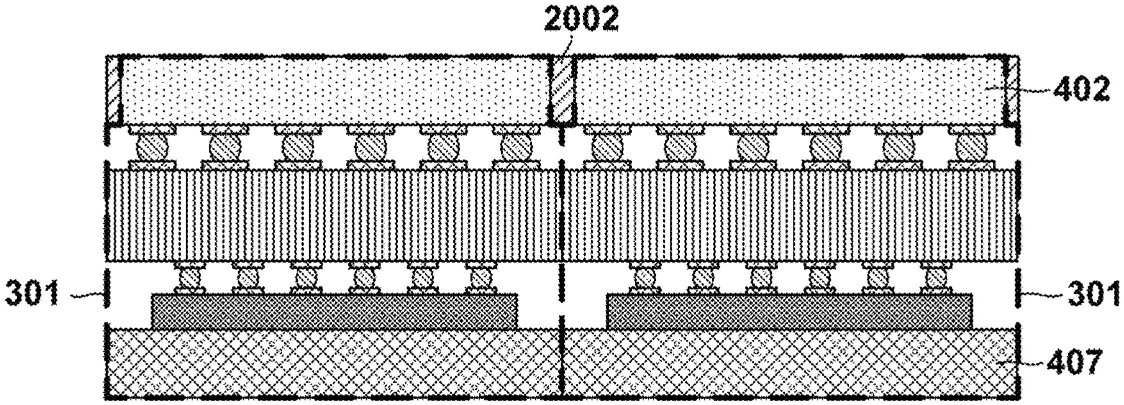

A method for manufacturing the radiation detection apparatus 104 according to another embodiment will be described with reference to FIG. 20B. Differences from the manufacturing method described with reference to FIGS. 19A and 19B will be described hereinafter. In the manufacturing method illustrated in FIG. 20B, the same sensor units 301 as those illustrated in FIGS. 19A and 19B may be prepared. Then, each of two adjacent sensor units 301, and an insulating layer 2002 disposed between the two adjacent sensor units 301, are bonded to each other by solid-phase bonding. In the example illustrated in FIG. 20B, the insulating layer 2002 is disposed between the semiconductor layers 402 of the two adjacent sensor units 301. As such, the semiconductor layer 402 in each of the two adjacent sensor units 301 and the insulating layer 2002 are bonded to each other by using solid-phase bonding. Instead of or in addition thereto, the insulating layer may be disposed between the interposers 404 of the two adjacent sensor units 301. Instead of or in addition thereto, the insulating layer may be disposed between the mounting boards 407 of the two adjacent sensor units 301. The insulating layer 2002 may be formed from silicon dioxide, for example. In the manufacturing method illustrated in FIG. 20B, another member may be used instead of the insulating layer 2002. In the manufacturing method illustrated in FIG. 20B, the interposers 404 of the two adjacent sensor units 301 may be bonded to each other by solid-phase bonding. Instead of or in addition thereto, the mounting boards 407 of the two adjacent sensor units 301 may be bonded to each other by solid-phase bonding.

Figure 21A:
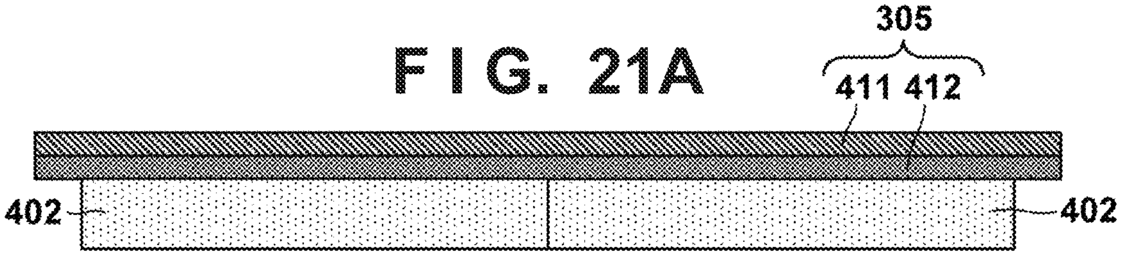
FIGS. 21A and 21B are cross-sectional views illustrating an example of a method for manufacturing a radiation detection apparatus according to some embodiments.

A method for manufacturing the radiation detection apparatus 104 according to another embodiment will be described with reference to FIGS. 21A and 21B. As illustrated in FIG. 21A, the substrate 305 and the semiconductor layers 402 are prepared. The substrate 305 may include the components described with reference to FIG. 13. The substrate 305 and the semiconductor layers 402 may be produced using an existing method, and thus the method for producing the substrate 305 and the semiconductor layers 402 will not be described in detail here.

The plurality of semiconductor layers 402 are then fixed to each other to form an array by bonding each of the plurality of semiconductor layers 402 and the substrate 305 to each other by using solid-phase bonding. In the method illustrated in FIGS. 21A and 21B, the semiconductor layers 402 are bonded to the substrate 305, with each semiconductor layer 402 being a unit structure.

The substrate 305 is provided in common for the plurality of semiconductor layers 402. The substrate 305 includes the conductive layer 412 that is bonded to the plurality of semiconductor layers 402, and the insulating layer 411 that is located on the opposite side of the plurality of semiconductor layers 402 with respect to the conductive layer 412. Instead, however, the substrate 305 may have a different configuration, and need not include the conductive layer 412, for example.

To suppress stress produced in the semiconductor layer 402, the solid-phase bonding between the plurality of semiconductor layers 402 and the substrate 305 may be performed at a low pressure. For example, the solid-phase bonding may be performed at a pressure where the plastic deformation amount of the semiconductor layer 402 is not greater than 10%.

Two adjacent semiconductor layers 402 among the plurality of semiconductor layers 402 may or may not be in contact with each other, and may or may not be bonded to each other. Two adjacent semiconductor layers 402 among the plurality of semiconductor layers 402 may be bonded to each other by solid-phase bonding, or may be bonded by a method other than solid-phase bonding.

Figure 21B:
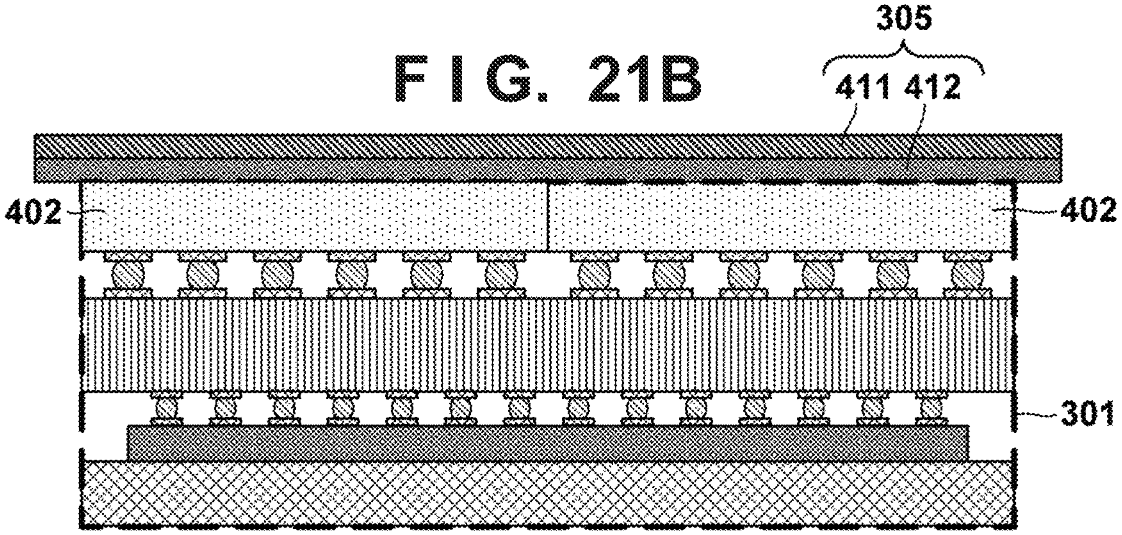

Then, as illustrated in FIG. 21B, the remaining components of the sensor unit 301 are produced. Thereafter, the radiation detection apparatus 104 is manufactured by performing the steps described above with reference to FIG. 18B.

In the process of FIG. 21A described above, the plurality of semiconductor layers 402 may be fixed to each other to form an array by bonding two semiconductor layers 402 adjacent to each other in the array by using solid-phase bonding, and then the plurality of semiconductor layers 402 may be bonded to the substrate 305. The bonding between the plurality of semiconductor layers 402 and the substrate 305 may be performed by solid-phase bonding, or by a method other than solid-phase bonding (fusion bonding, liquid-solid reactive bonding, or the like). In this variation, the plurality of semiconductor layers 402 are bonded to each other, and thus the substrate 305 and the plurality of semiconductor layers 402 need not be bonded to each other, and may simply be in contact with each other. Instead, however, the radiation detection apparatus 104 need not include the substrate 305.

In the process illustrated in FIG. 21A or the variation described above, the insulating layer may be disposed between two adjacent semiconductor layers 402, instead of the two adjacent semiconductor layers 402 being bonded to each other. As described above with reference to FIG. 20A, the insulating layer may be formed to cover at least a part of the side surfaces of each of the semiconductor layers 402, and then the insulating layers may be bonded to each other by solid-phase bonding. Instead, however, each of the two adjacent semiconductor layers 402, and the insulating layer disposed between the two adjacent semiconductor layers 402, may be bonded to each other by solid-phase bonding, as described above with reference to FIG. 20B.

The foregoing embodiments have described the radiation detection apparatus 104 in the context of the CT apparatus 100. Instead, however, the radiation detection apparatus 104 may be used in another apparatus, such as a fluoroscopic diagnostic apparatus, an object inspection apparatus, or the like, for example. Additionally, the foregoing embodiments have described the radiation detection apparatus 104 which detects radiation. However, the embodiments are not limited thereto, and the foregoing embodiments can be applied, for example, to a radiation detector that detects γ-rays, particle radiation, or the like. Additionally, the foregoing embodiments can also be applied in a diagnostic radiology apparatus, other than the CT apparatus 100, that is provided with the radiation detection apparatus 104. In this case, the diagnostic radiology apparatus includes, for example, a Positron Emission Tomography (PET) apparatus, a Single Photon Emission Computed Tomography (SPECT) apparatus, and the like.

Variations on the radiation detection apparatus 104 will be described with reference to FIGS. 22A to 22D. The radiation detection apparatus 104 described above had an arc shape.

Figure 22A:
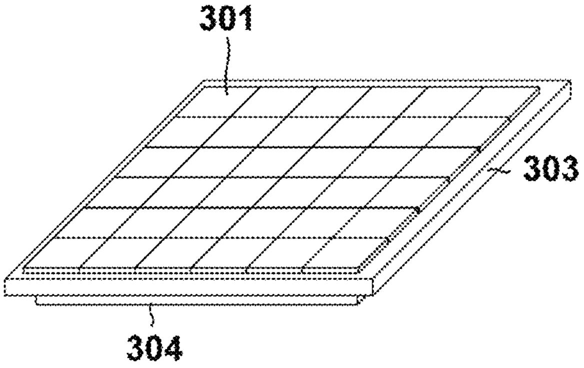
FIGS. 22A to 22D are schematic diagrams illustrating an example of the arrangement of a sensor unit according to some embodiments.
Figure 22B:
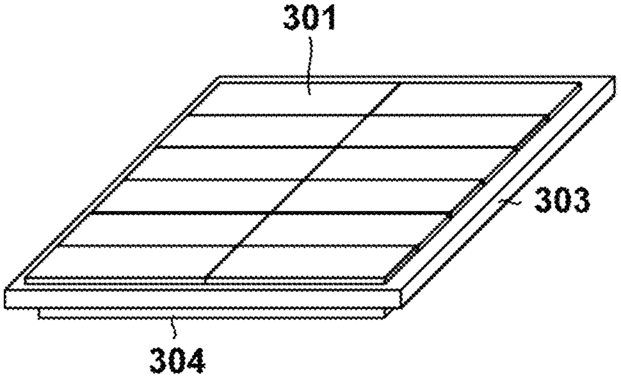
Figure 22C:
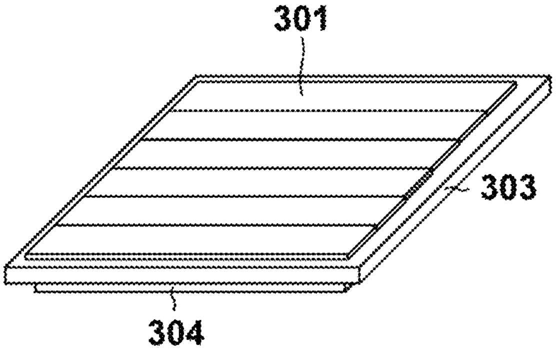
Figure 22D:
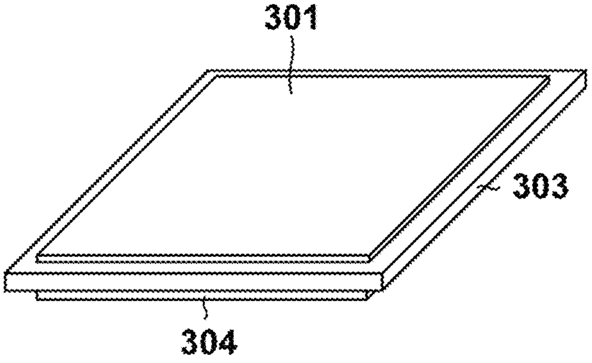

Instead, however, the radiation detection apparatus 104 may have a planar shape, as illustrated in each of FIGS. 22A to 22D. For the sake of simplicity, FIGS. 22A to 22D illustrate only the sensor units 301, the frame 303, and the circuit board 304. In FIG. 22A, the plurality of sensor units 301 are disposed so as to form a 6×6 two-dimensional array. One frame 303 and one circuit board 304 are disposed in common for the plurality of sensor units 301. In FIG. 22B, the plurality of sensor units 301 are disposed so as to form a 6×2 two-dimensional array. In FIG. 22C, the plurality of sensor units 301 are disposed so as to form a 6×1 one-dimensional array. In FIG. 22D, only a single sensor unit 301 is disposed. In this case, the sensor unit 301 may include the plurality of semiconductor layers 402 disposed so as to form an array, as described above with reference to FIG. 6.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2023-128000, filed Aug. 4, 2023, Japanese Patent Application No. 2023-128003, filed Aug. 4, 2023, Japanese Patent Application No. 2024-049991 filed Mar. 26, 2024, which are hereby incorporated by reference herein in their entirety.

What is claimed is:

1. A radiation detection apparatus comprising:

a plurality of unit structures, each unit structure of the plurality of unit structures having a semiconductor layer that converts radiation into a charge, the plurality of unit structures being arranged to form an array;

a coupling member that couples two of the plurality of unit structures adjacent to each other in the array; and an integrated circuit, wherein the coupling member is formed from a material capable of being used as a vapor deposition material, and each unit structure of the plurality of unit structures further includes a mounting board on which is mounted the integrated circuit that processes a signal based on the charge resulted from radiation converted by the semiconductor layer.

2. The radiation detection apparatus according to claim 1, wherein the coupling member includes one or more of parylene, polyethylene, polytetrafluoroethylene, polyimide, polyamide, polyurea, and polyurethane.

3. The radiation detection apparatus according to claim 1, wherein the coupling member includes one or more of silicon oxide, aluminum oxide, and silicon nitride.

4. The radiation detection apparatus according to claim 1, wherein the coupling member includes one or more of TEOS, TMB, TEB, TMP, TMOP, TEOP, TriMS, and MTMS.

5. The radiation detection apparatus according to claim 1, wherein the coupling member couples the semiconductor layers of two adjacent ones of the unit structures in the array with each other.

6. The radiation detection apparatus according to claim 1, wherein each unit structure of the plurality of unit structures further includes an interposer located between the semiconductor layer and the mounting board, and in a plan view of a surface on which radiation is incident, the semiconductor layer is larger than the mounting board and the interposer.

7. The radiation detection apparatus according to claim 1, wherein the coupling member covers a side surface of the semiconductor layer and at least a part of a bottom surface of the semiconductor layer.

8. The radiation detection apparatus according to claim 1, wherein the coupling member is elastic.

9. The radiation detection apparatus according to claim 1, further comprising:

a plurality of sensor modules arranged in an arc, wherein each sensor module of the plurality of sensor modules includes the plurality of unit structures, and each unit structure of the plurality of unit structures is a sensor unit.

10. The radiation detection apparatus according to claim 1, wherein the plurality of unit structures is a plurality of sensor units, and the radiation detection apparatus is arranged to form a two-dimensional array.

11. A system comprising:

the radiation detection apparatus according to claim 1, wherein the radiation detection apparatus is a photon counting-type radiation detection apparatus;

at least one processor;

and a memory coupled to the at least one processor, the memory having instructions that, when executed by the at least one processor, causes the at least one processor to process a signal output from the radiation detection apparatus to generate image data using a result of counting radiation photons produced by radiation transmitted through a subject.

12. A radiation detection apparatus comprising:

a plurality of unit structures, each unit structure of the plurality of unit structures having a semiconductor layer that converts radiation into a charge, the plurality of unit structures being arranged to form an array;

a coupling member that couples two of the plurality of unit structures adjacent to each other in the array, wherein the coupling member is formed from a material capable of being used as a vapor deposition material;

a mounting board provided in common for the plurality of unit structures; and an integrated circuit that processes a signal based on the charge resulted from radiation converted by the semiconductor layer, the integrated circuit being mounted on the mounting board.

13. The radiation detection apparatus according to claim 12, further comprising:

an interposer provided in common for the plurality of unit structures, the interposer being located between the semiconductor layer and the mounting board.

14. The radiation detection apparatus according to claim 12, further comprising:

a plurality of sensor modules arranged in an arc, wherein each sensor module of the plurality of sensor modules includes the plurality of unit structures, and each unit structure of the plurality of unit structures is a sensor unit.

15. The radiation detection apparatus according to claim 12, wherein the plurality of unit structures is a plurality of sensor units, and the radiation detection apparatus is arranged to form a two-dimensional array.

16. A system comprising;

the radiation detection apparatus according to claim 12, wherein the radiation detection apparatus is a photon counting-type radiation detection apparatus;

at least one processor; and a memory coupled to the at least one processor, the memory having instructions that, when executed by the at least one processor, causes the at least one processor to process a signal output from the radiation detection apparatus to generate image data using a result of counting radiation photons produced by radiation transmitted through a subject.

17. A radiation detection apparatus comprising:

a substrate;

a plurality of unit structures, each unit structure of the plurality of unit structures having a semiconductor layer that converts radiation into a charge, the plurality of unit structures being arranged to form an array; and two members forming an interface and bonded by solid-phase bonding in at least one of:

between each of the plurality of unit structures and the substrate provided in common for the plurality of unit structures;

between two of the plurality of unit structures adjacent to each other in the array; and between each of two of the plurality of unit structures adjacent to each other in the array and a member disposed between the two of the plurality of unit structures adjacent to each other.

18. The radiation detection apparatus according to claim 17, wherein the two members forming the interface are bonded by the solid-phase bonding by a cohesive force among atoms.

19. A method for manufacturing a radiation detection apparatus, the method comprising:

fixing a plurality of unit structures, each unit structure of the plurality of unit structures having a semiconductor layer that converts radiation into a charge, to each other to form an array, wherein the fixing the plurality of unit structures includes at least one of:

bonding each unit structure of the plurality of unit structures and a substrate provided in common for the plurality of unit structures by using solid-phase bonding;

bonding two of the plurality of unit structures adjacent to each other in the array by using solid-phase bonding; and bonding each of two of the plurality of unit structures adjacent to each other in the array, and a member disposed between the two of the plurality of unit structures adjacent to each other, by using solid-phase bonding.

20. A non-transitory computer readable storage medium having stored therein a program for causing a computer to execute the method according to claim 19.

* * * * *